(12) United States Patent
Czernik et al.

(10) Patent No.: US 8,469,254 B2
(45) Date of Patent: Jun. 25, 2013

(54) SURGICAL INSTRUMENT HAVING A DRIVE ASSEMBLY

(75) Inventors: Roman Czernik, Trumbull, CT (US); Steven Bartlett, Prospect, CT (US)

(73) Assignee: Covidien LP, Mansfield, MA (US)

( * ) Notice: Subject to any disclaimer, the term of this patent is extended or adjusted under 35 U.S.C. 154(b) by 387 days.

(21) Appl. No.: 12/692,052

(22) Filed: Jan. 22, 2010

(65) Prior Publication Data
US 2011/0180585 A1 Jul. 28, 2011

(51) Int. Cl.
*A61B 17/068* (2006.01)

(52) U.S. Cl.
USPC .................. 227/176.1; 227/19; 227/175.1

(58) Field of Classification Search
USPC ............... 227/19, 175.1, 176.1, 180.1
See application file for complete search history.

(56) References Cited

U.S. PATENT DOCUMENTS

| | | | |
|---|---|---|---|
| 5,389,098 A | 2/1995 | Tsuruta et al. | |
| 5,782,397 A | 7/1998 | Koukline | |
| 6,582,452 B2 | 6/2003 | Coleman et al. | |
| 6,669,714 B2 | 12/2003 | Coleman et al. | |
| 6,786,382 B1 | 9/2004 | Hoffman | |
| 6,953,139 B2 | 10/2005 | Milliman et al. | |
| 7,097,089 B2 | 8/2006 | Marczyk | |
| 7,143,924 B2 | 12/2006 | Scirica et al. | |
| 7,172,104 B2 | 2/2007 | Scirica et al. | |
| 7,225,963 B2 | 6/2007 | Scirica | |
| 7,354,447 B2 | 4/2008 | Shelton, IV et al. | |
| 7,407,078 B2 * | 8/2008 | Shelton et al. | 227/180.1 |
| 7,431,188 B1 | 10/2008 | Marczyk | |
| 7,481,348 B2 | 1/2009 | Marczyk | |
| 7,543,730 B1 | 6/2009 | Marczyk | |
| 2005/0103819 A1 * | 5/2005 | Racenet et al. | 227/175.1 |
| 2005/0178813 A1 | 8/2005 | Swayze et al. | |
| 2005/0184123 A1 | 8/2005 | Scirica | |
| 2005/0184124 A1 | 8/2005 | Scirica et al. | |
| 2005/0184125 A1 | 8/2005 | Marczyk | |
| 2005/0279804 A1 | 12/2005 | Scirica et al. | |
| 2006/0226195 A1 | 10/2006 | Scirica et al. | |

(Continued)

FOREIGN PATENT DOCUMENTS

EP 1 479 348 A1 11/2004
EP 1621139 A 2/2006
(Continued)

OTHER PUBLICATIONS

European Search Report for EP 09252246.5-1269 date of completion is Nov. 24, 2009 (3 pages).

(Continued)

*Primary Examiner* — M. Alexandra Elve
*Assistant Examiner* — Nathaniel Chukwurah

(57) ABSTRACT

A surgical instrument comprising a handle assembly, an elongate member extending from the handle assembly, a loading unit extending from the elongate member, a drive assembly operatively associated with the handle assembly and configured to translate through the loading unit upon actuation of the handle assembly, the drive assembly including a drive beam and an end member projecting distally from the drive beam, wherein a portion of the end member has a different thickness than the drive beam and a first jaw and a second jaw extending from the loading unit and operatively coupled to the drive assembly, at least one of the first jaw and the second jaw movable in response to translation of the drive assembly.

19 Claims, 35 Drawing Sheets

U.S. PATENT DOCUMENTS

| | | |
|---|---|---|
| 2006/0289602 A1 | 12/2006 | Wales et al. |
| 2007/0045380 A1 | 3/2007 | Mastri et al. |
| 2007/0102472 A1 | 5/2007 | Shelton, IV |
| 2007/0102476 A1 | 5/2007 | Shelton, IV et al. |
| 2007/0170225 A1 | 7/2007 | Shelton, IV et al. |
| 2007/0175948 A1 | 8/2007 | Scirica et al. |
| 2007/0175961 A1 | 8/2007 | Shelton, IV et al. |
| 2007/0187454 A1 | 8/2007 | Scirica |
| 2008/0017693 A1 | 1/2008 | Mastri et al. |
| 2008/0029576 A1 | 2/2008 | Shelton et al. |
| 2008/0029577 A1 | 2/2008 | Shelton et al. |
| 2008/0041916 A1 | 2/2008 | Milliman et al. |
| 2008/0083807 A1 | 4/2008 | Beardsley et al. |
| 2008/0083808 A1 | 4/2008 | Scirica |
| 2008/0083809 A1 | 4/2008 | Scirica |
| 2008/0083810 A1 | 4/2008 | Marczyk |
| 2008/0083811 A1 | 4/2008 | Marczyk |
| 2008/0083812 A1 | 4/2008 | Scirica |
| 2008/0179374 A1 | 7/2008 | Beardsley et al. |
| 2008/0223903 A1 | 9/2008 | Marczyk |
| 2008/0265001 A1 | 10/2008 | Green et al. |
| 2008/0302854 A1 | 12/2008 | Rethy et al. |
| 2008/0308605 A1 | 12/2008 | Scirica |
| 2009/0001129 A1 | 1/2009 | Marczyk |

FOREIGN PATENT DOCUMENTS

| | | |
|---|---|---|
| EP | 1 767 156 A1 | 3/2007 |
| EP | 1908414 A | 4/2008 |
| EP | 2 116 196 A3 | 11/2009 |

OTHER PUBLICATIONS

European Search Report for EP 11250056.6-2310 date of completion is May 2, 2011 (3 pages).

* cited by examiner

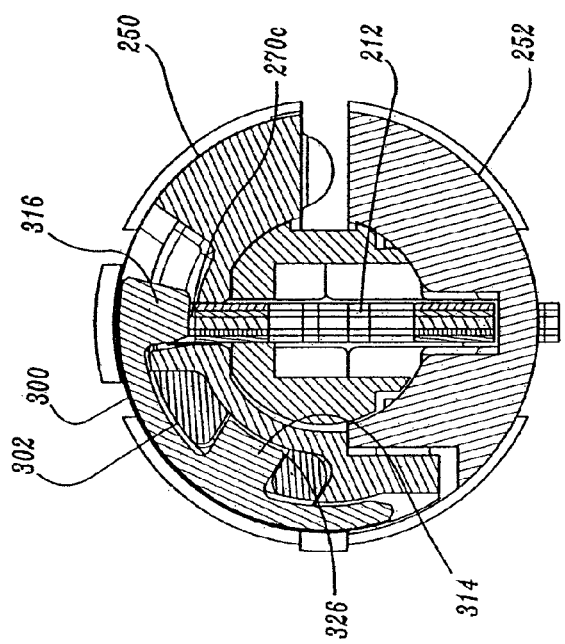
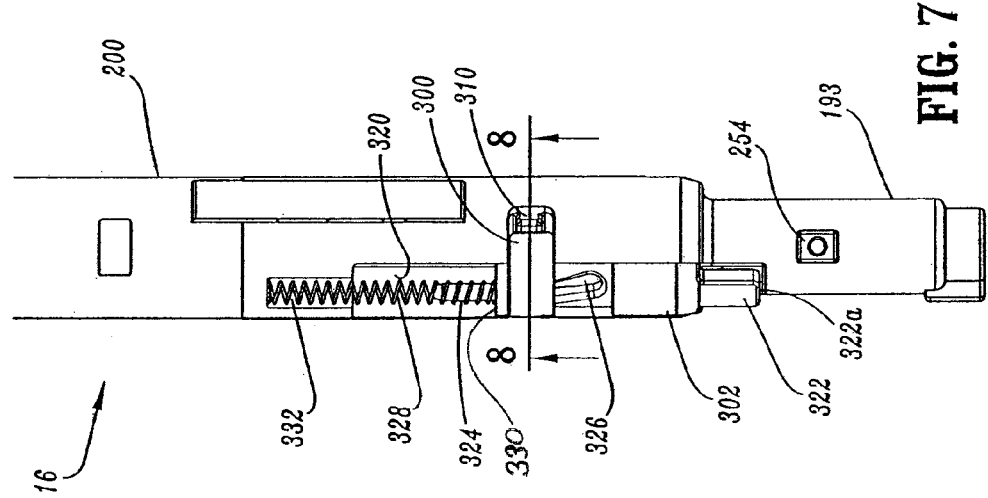
FIG. 8
FIG. 7

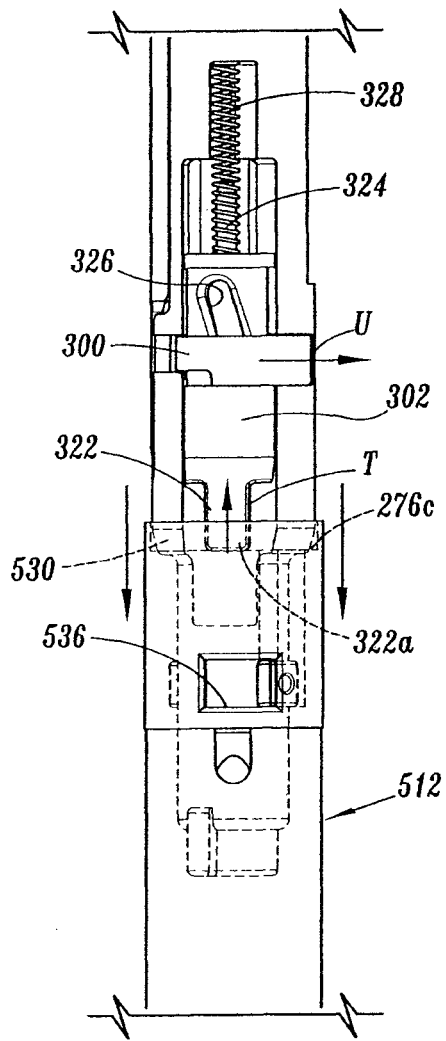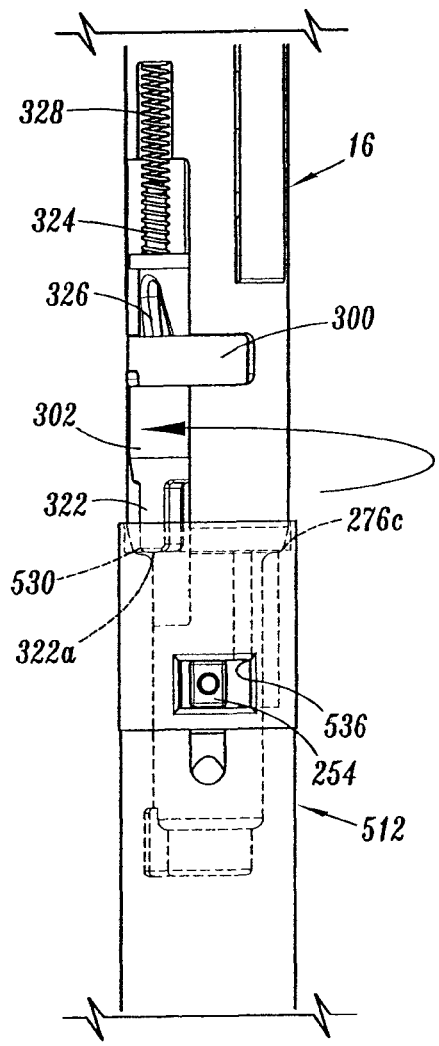
FIG. 14  FIG. 15

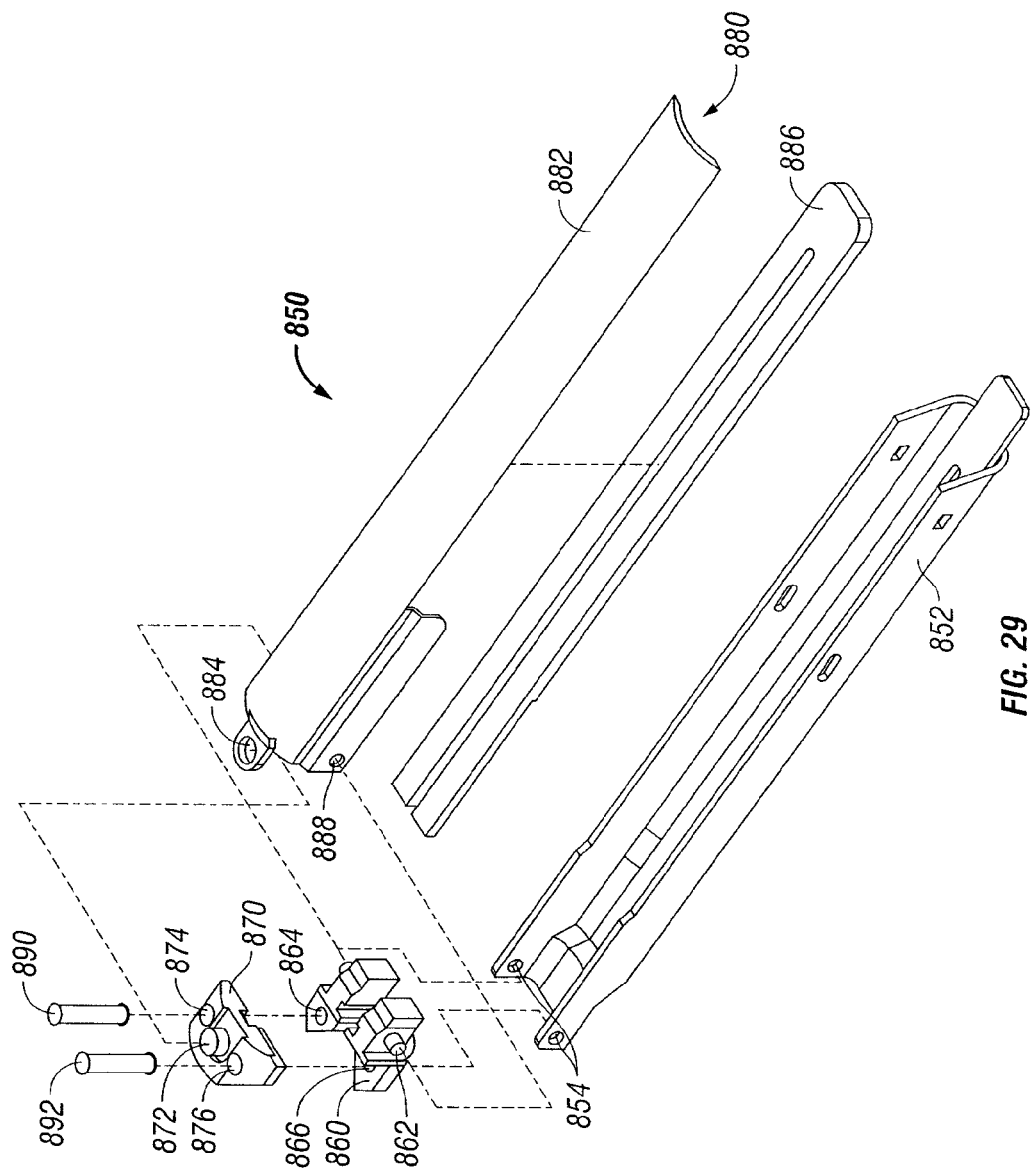

SURGICAL INSTRUMENT HAVING A DRIVE ASSEMBLY

BACKGROUND

1. Technical Field

The present disclosure relates to a surgical instrument and disposable loading unit including a plastic surface thereon. More particularly, the present disclosure relates to a surgical instrument which includes a plastic surface on at least one of a closure apparatus and a contact surface of a tool assembly.

2. Background of the Related Art

Surgical devices wherein tissue is first grasped or clamped between opposing jaw structure and then joined by surgical fasteners are well known in the art. In some instruments, a knife is provided to cut the tissue which has been joined by the fasteners. The fasteners are typically in the form of surgical staples but two part polymeric fasteners can also be utilized.

Instruments for this purpose may include two elongated members which are respectively used to capture or clamp tissue. Typically, one of the members carries a staple cartridge that houses a plurality of staples arranged in at least two lateral rows while the other member has an anvil that defines a surface for forming the staple legs as the staples are driven from the staple cartridge. In some instruments, the closure of the two elongated members, or tool assembly, is affected by actuation of a movable handle which moves a drive beam having a closure apparatus thereon into a contact surface of a tool assembly, thus approximating the members of the tool assembly.

SUMMARY

There is disclosed a surgical instrument having a handle assembly, an elongate member extending from the handle assembly, a loading unit extending from the elongate member, a drive assembly operatively associated with the handle assembly and configured to translate through the loading unit upon actuation of the handle assembly and a first jaw and a second jaw operatively coupled to the drive assembly, at least one of the first jaw and the second jaw movable in response to translation of the drive assembly. The drive assembly includes a drive beam and an end member projecting distally from the drive beam where a portion of the end member has a different thickness than the drive beam.

In one embodiment the end member may include a flange extending laterally from the end member and oriented substantially perpendicular to the end member.

In another embodiment the end member may include a cap which may be attached to the end member through various methods including but not limited to, e.g., brazing In a further embodiment portions of the end member may have different thicknesses, e.g. a first portion of the end member may have a first thickness and a remaining second portion of the end member may have a second thickness where second thickness is different than the first thickness so as to create a flange There is also disclosed a number of methods for structurally reinforcing an end member of a drive beam In one embodiment the drive beam end member may be structurally reinforced by bending a portion of the end member from a first state to a second state, the first state being substantially parallel to the end member and the second state being at an angle to the end member. The bend may alternatively be substantially perpendicular to the end member.

In another embodiment the end member may be structurally reinforced by attaching a cap. The cap may be substantially U-shaped, may have the same length as the end member and may include a slot dimensioned to receive the end member.

In a further embodiment the end member may also be structurally reinforced by reducing the thickness of the drive beam and a first portion of the end member such that a flange is created by the difference between the thickness of the remaining second portion of the end member and the reduced thickness of the first portion of the end member.

DESCRIPTION OF THE DRAWINGS

Various embodiments of the presently disclosed surgical instrument are disclosed herein with reference to the drawings, wherein:

FIG. 7 is a top view of the proximal end of the loading unit proximal body portion shown in FIG. 1A with the locking mechanism in its locked position;

FIG. 8 is a cross-sectional view taken along section lines 8-8 of FIG. 7;

FIG. 14 is a top view of the proximal end of the loading unit and the distal end of the surgical instrument shown in FIG. 12 after the loading unit has been advanced linearly but prior to locking the loading unit to the surgical instrument;

FIG. 15 is a top view of the proximal end of the loading unit and the distal end of the surgical instrument shown in FIG. 13 after the loading unit has been advanced linearly and rotatably locked onto the surgical instrument;

FIG. 29 is an assembly view of the tool assembly of FIG. 28;

DETAILED DESCRIPTION OF EMBODIMENTS

Figure 1:
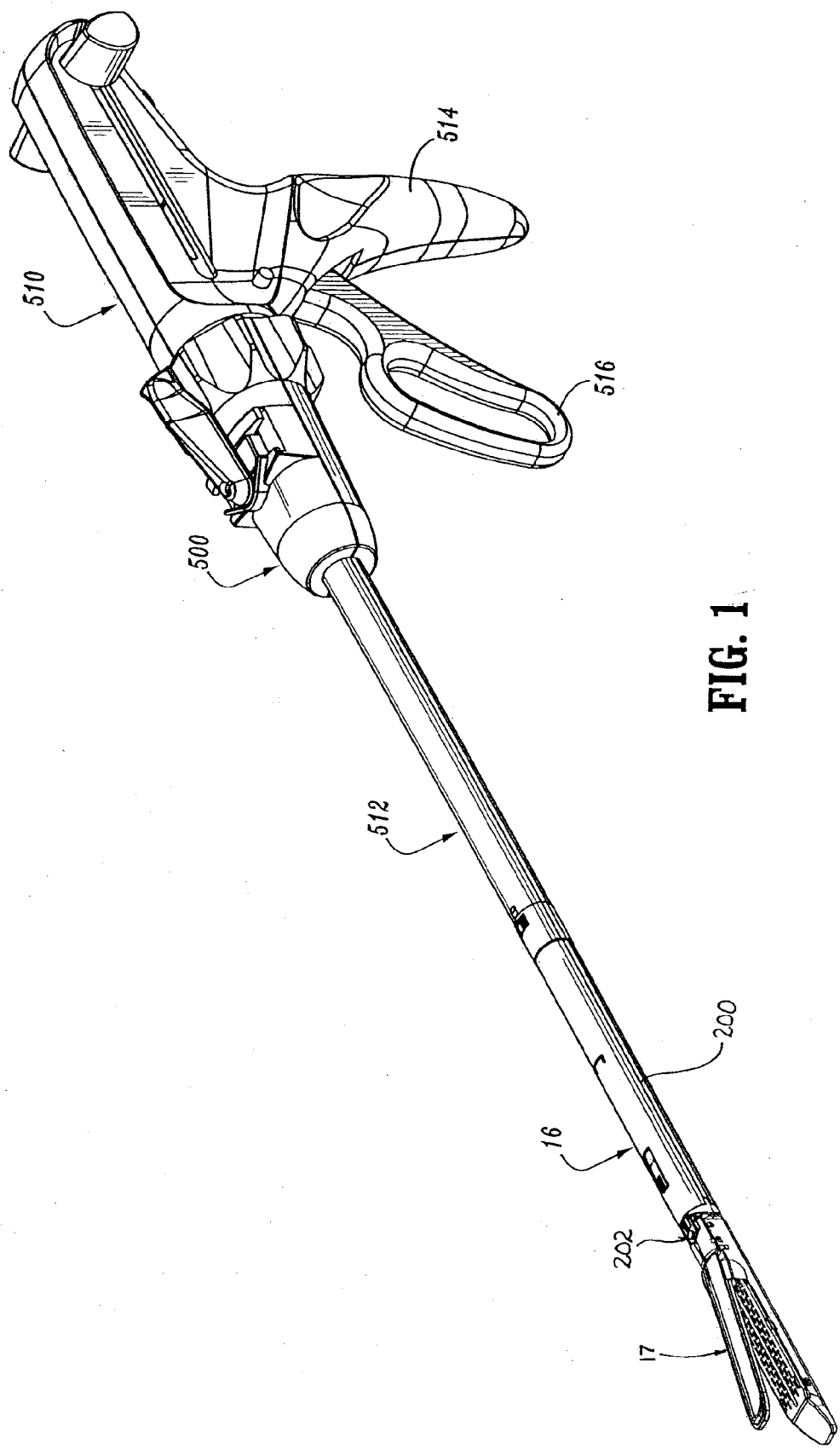
FIG. 1 is a side perspective view from the distal end of one embodiment of the presently disclosed surgical instrument with articulating tool assembly.

Embodiments of the presently disclosed surgical instrument and loading unit will now be described in detail with reference to the drawings, in which like reference numerals designate identical or corresponding elements in each of the several views.

Referring to FIG. 1, surgical instrument 500 includes a handle portion 510, a body portion 512, and a loading unit 16. Handle portion 510 includes a stationary handle 514 and a movable handle or trigger 516. Movable handle 516 is movable in relation to stationary handle 514 to advance a control rod 520 which projects from the distal end of body portion 512. Handle portion 510 and body portion 512 may be constructed in the manner disclosed in U.S. Pat. No. 6,330,965 which is hereby incorporated herein in its entirety by reference. Alternately, other surgical instruments can be used with loading unit 16 to perform endoscopic surgical procedures.

Figure 1A:
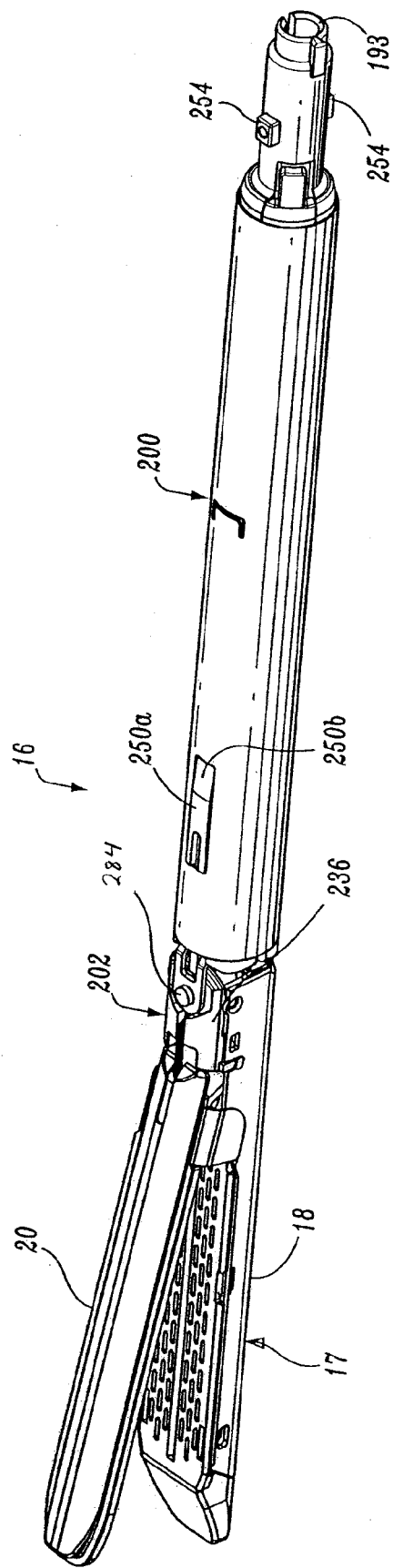
FIG. 1A is a side perspective view from the proximal end of a loading unit of the surgical instrument shown in FIG. 1 including the tool assembly.
Figure 11:
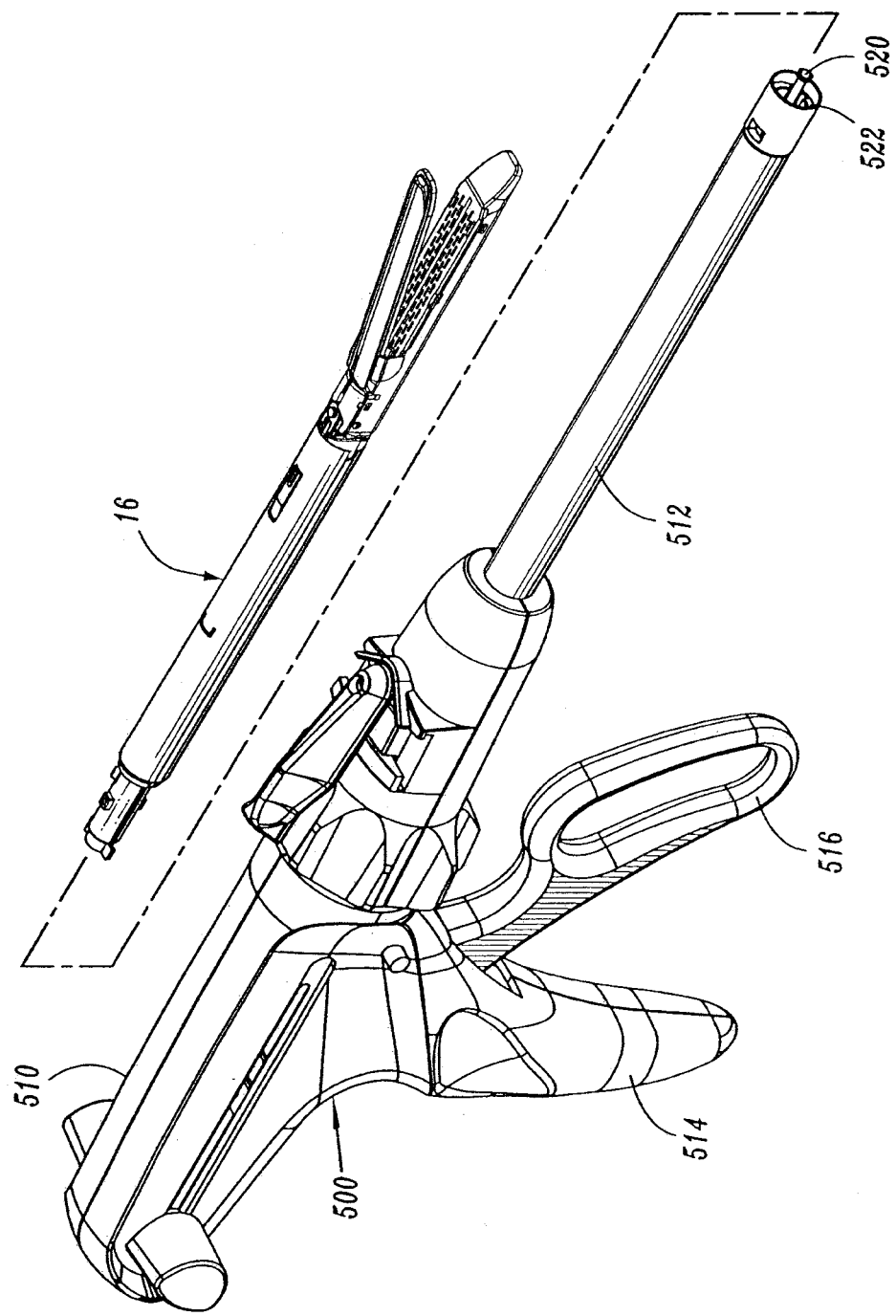
FIG. 11 is a side perspective view of the loading unit and surgical instrument shown in FIG. 1 prior to attachment of the loading unit to the surgical instrument.
Figure 12:
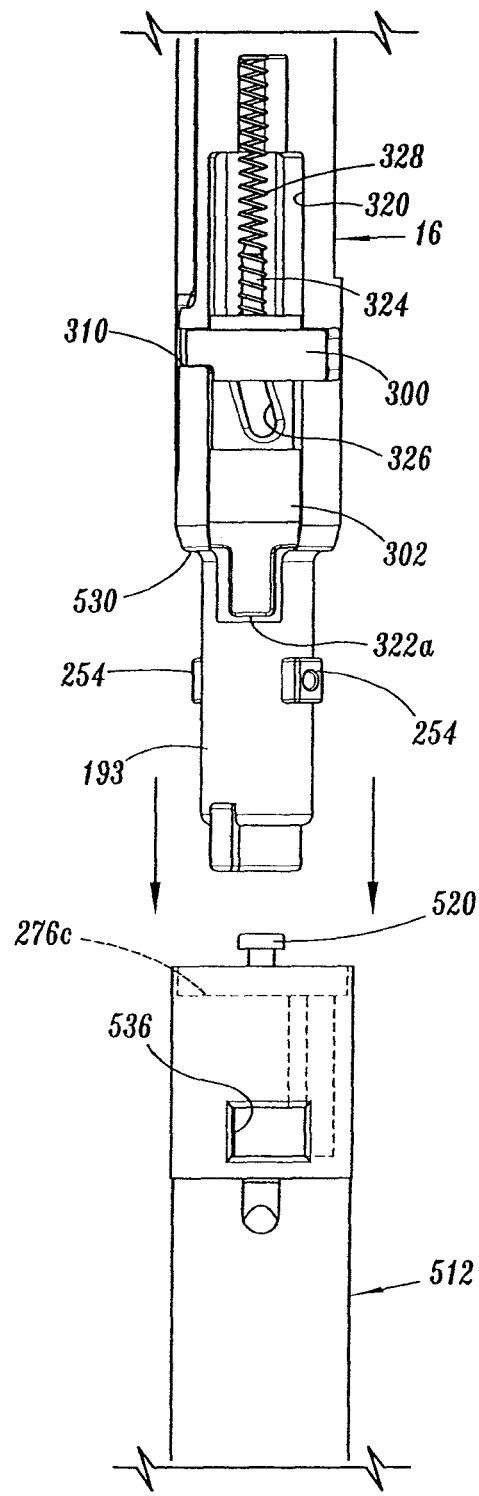
FIG. 12 is a top view of the proximal end of the loading unit and the distal end of the surgical instrument shown in FIG. 11 prior to attachment to the distal end of the surgical instrument.
Figure 13:
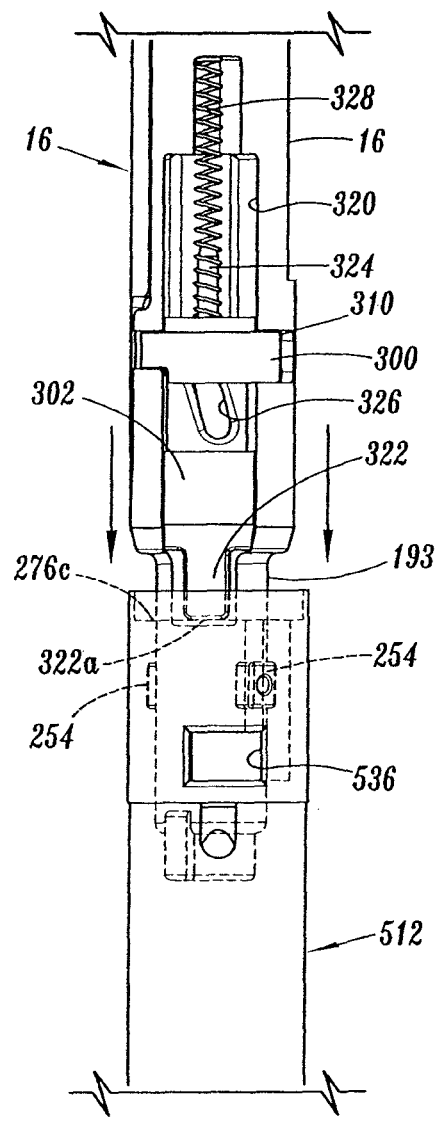
FIG. 13 is a top view of the proximal end of the loading unit shown in FIG. 11 as the loading unit is advanced linearly into the distal end of the surgical instrument.

Referring to FIGS. 1 and 1A, briefly, loading unit 16 includes a tool assembly 17, a proximal body portion 200 and a mounting assembly 202. Body portion 200 has a proximal end adapted to releasably engage the distal end of a surgical instrument 500 (FIG. 11) in the manner to be discussed in detail below. Mounting assembly 202 is pivotally secured to a distal end of body portion 200 and is fixedly secured to a proximal end of tool assembly 17. Pivotal movement of mounting assembly 202 about an axis perpendicular to a longitudinal axis of body portion 200 affects articulation of tool assembly 17 between a non-articulated position in which the longitudinal axis of tool assembly 17 is aligned with the longitudinal axis of body portion 200 and an articulated position in which the longitudinal axis of tool assembly 17 is disposed at an angle to the longitudinal axis of body portion 200.

Figure 2:
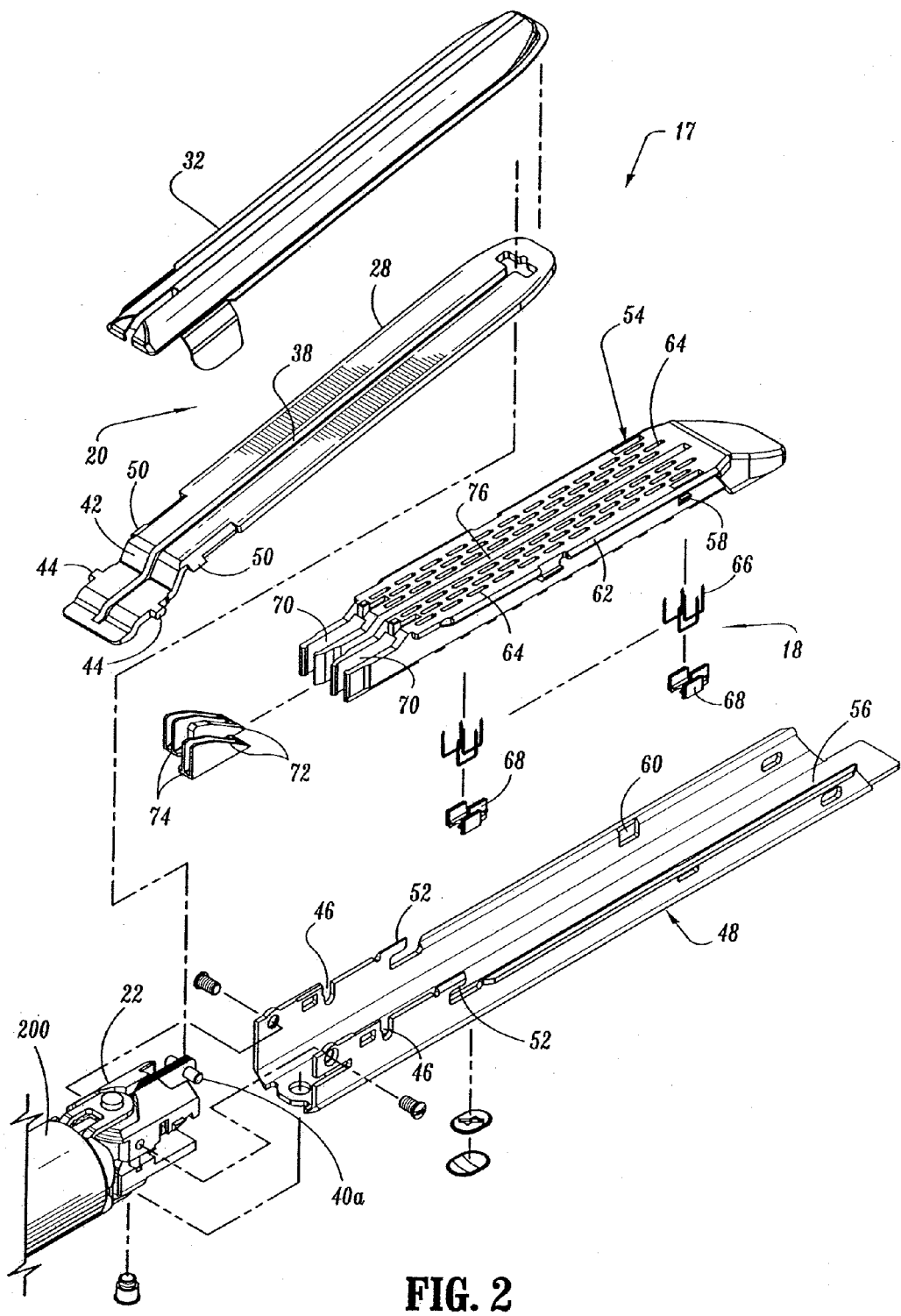
FIG. 2 is a side perspective view of the distal end of mounting assembly and tool assembly, with parts separated, of the loading unit of the surgical instrument shown in FIG. 1.
Figure 3:
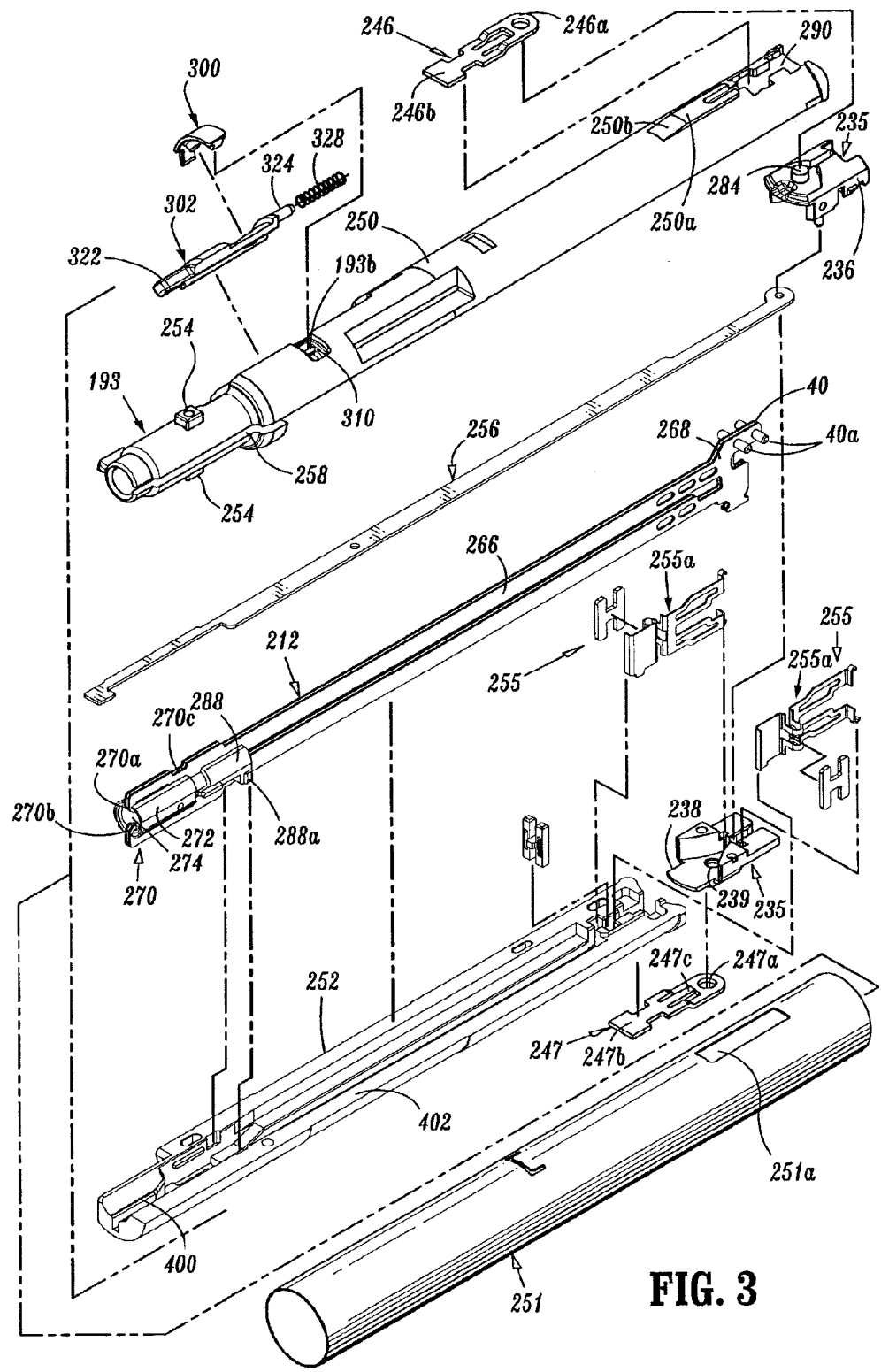
FIG. 3 is a side perspective view of the mounting assembly and the proximal body portion of the loading unit shown in FIG. 1A with parts separated.
Figure 4:
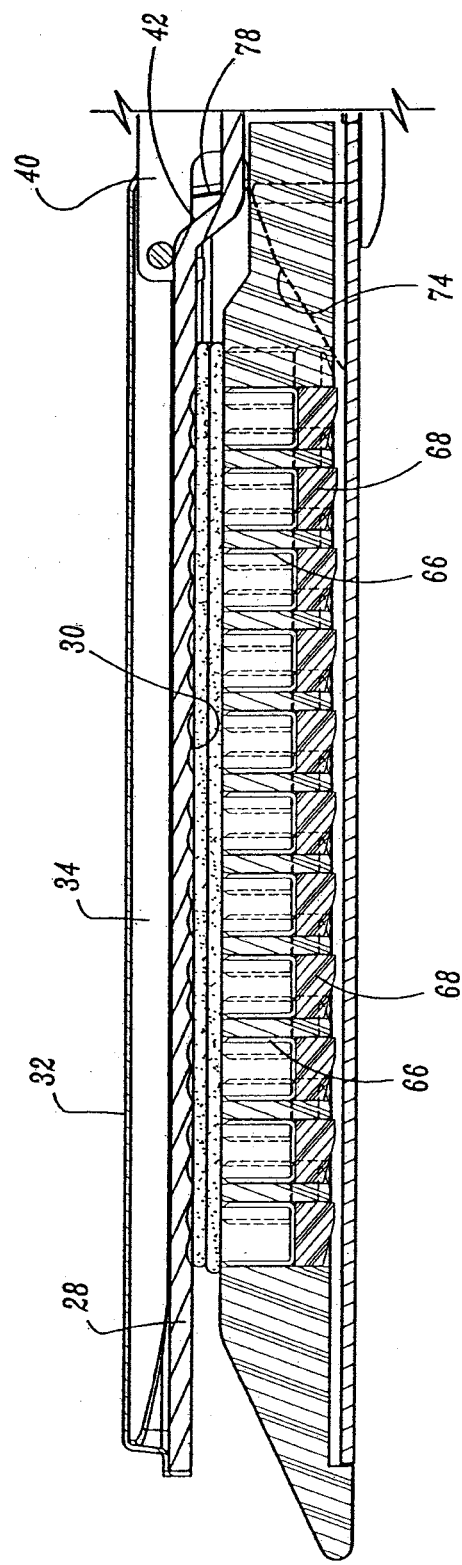
FIG. 4 is a side cross-sectional view of the tool assembly of the loading unit shown in FIG. 1A.

Referring to FIGS. 2-4, tool assembly 17 includes a cartridge assembly 18 and an anvil assembly 20. Anvil assembly 20 includes an anvil portion 28 having a plurality of staple deforming concavities 30 (FIG. 4) and a cover plate 32 secured to a top surface of anvil portion 28. Cover plate 32 and anvil portion 28 define a cavity 34 (FIG. 4) therebetween which is dimensioned to receive a distal end of a drive assembly 212 (FIG. 3). Cover plate 32 encloses the distal end of drive assembly 212 to prevent pinching of tissue during actuation of loading unit 16. A longitudinal slot 38 extends through anvil portion 28 to facilitate passage of a retention flange 40 of drive assembly 212. A camming surface 42 formed on anvil portion 28 is positioned to engage a pair of cam members 40a supported on retention flange 40 of drive assembly 212 to effect approximation of the anvil and cartridge assemblies. A pair of pivot members 44 are formed. A pair of stabilizing members 50 engage a respective shoulder 52 formed on carrier 48 to prevent anvil portion 28 from sliding axially in relation to staple cartridge 54 as camming surface 42 is pivoted about pivot members 44.

Cartridge assembly 18 includes carrier 48 which defines an elongated support channel 56 which is dimensioned and configured to receive staple cartridge 54. Corresponding tabs 58 and slots 60 formed along staple cartridge 54 and elongated support channel 56, respectively, function to retain staple cartridge 54 at a fixed location within support channel 56. A pair of support struts 62 formed on staple cartridge 54 are positioned to rest on side walls of carrier 48 to further stabilize staple cartridge 54 within support channel 56. Carrier 48 has slots 46 for receiving pivot members 44 of anvil portion 28 and allowing anvil portion 28 to move between spaced and approximated positions.

Staple cartridge 54 includes retention slots 64 (FIG. 2) for receiving a plurality of staples or fasteners 66 and pushers 68. A plurality of laterally spaced apart longitudinal slots 70 extend through staple cartridge 54 to accommodate upstanding cam wedges 72 of an actuation sled 74 (FIG. 2). A central longitudinal slot 76 extends along substantially the length of staple cartridge 54 to facilitate passage of a knife blade 78 (FIG. 4). During operation of surgical instrument 10, drive assembly 212 abuts actuation sled 74 and pushes actuation sled 74 through longitudinal slots 70 of staple cartridge 54 to advance cam wedges 72 into sequential contact with pushers 68. Pushers 68 translate vertically along cam wedges 72 within fastener retention slots 64 and urge fasteners 66 from retention slots 64 into staple deforming cavities 30 (FIG. 4) of anvil assembly 20.

Referring to FIG. 3, mounting assembly 235 includes an upper mounting portion 236 and a lower mounting portion 238. A centrally located pivot member 284 extends from upper mounting portion 236 through a respective opening 246a formed in a first coupling member 246. Lower mounting portion 238 includes a bore 239 for receiving pivot member 284 (see FIG. 3F). Pivot member 284 extends through bore 239 and opening 247a of a second coupling member 247. Each of coupling members 246, 247 includes an interlocking proximal portion 246b, 247b configured to be received in grooves 290 formed in the distal end of an inner housing which is formed from upper and lower housing halves 250 and 252. Coupling members 246, 247 retain mounting assembly 235 and upper and lower housing halves 250 and 252 in a longitudinally fixed position in relation to each other while permitting pivotal movement of mounting assembly 235 in relation thereto.

Figure 3A:
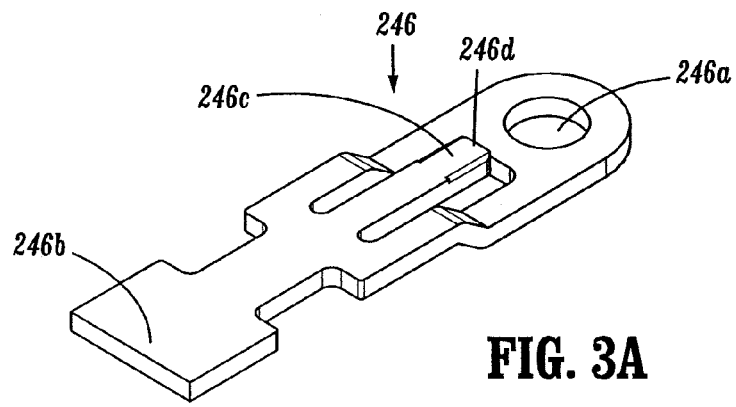
FIG. 3A is a side perspective view of a coupling member of the surgical instrument shown in FIG. 1.
Figure 3B:
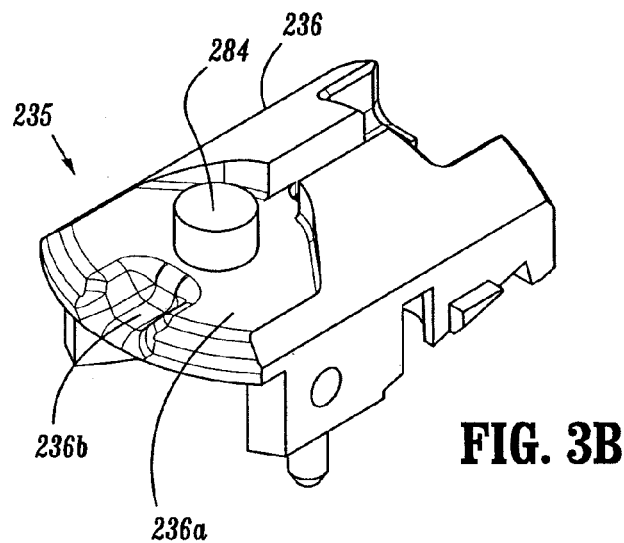
FIG. 3B is a side perspective view of an upper mounting portion of the mounting assembly of the loading unit of the surgical instrument shown in FIG. 1.
Figure 3C:
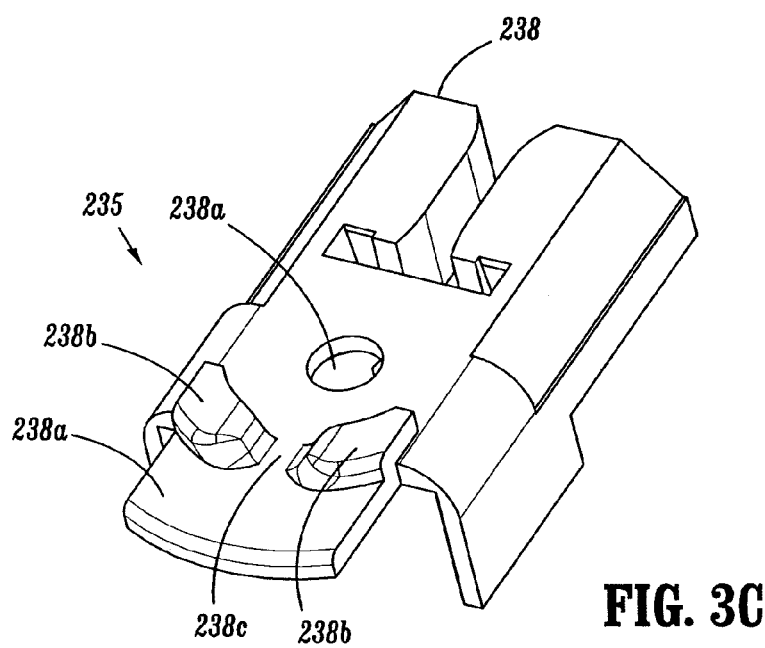
FIG. 3C is a side perspective view of a lower mounting portion of the mounting assembly of the loading unit of the surgical instrument shown in FIG. 1.
Figure 3D:
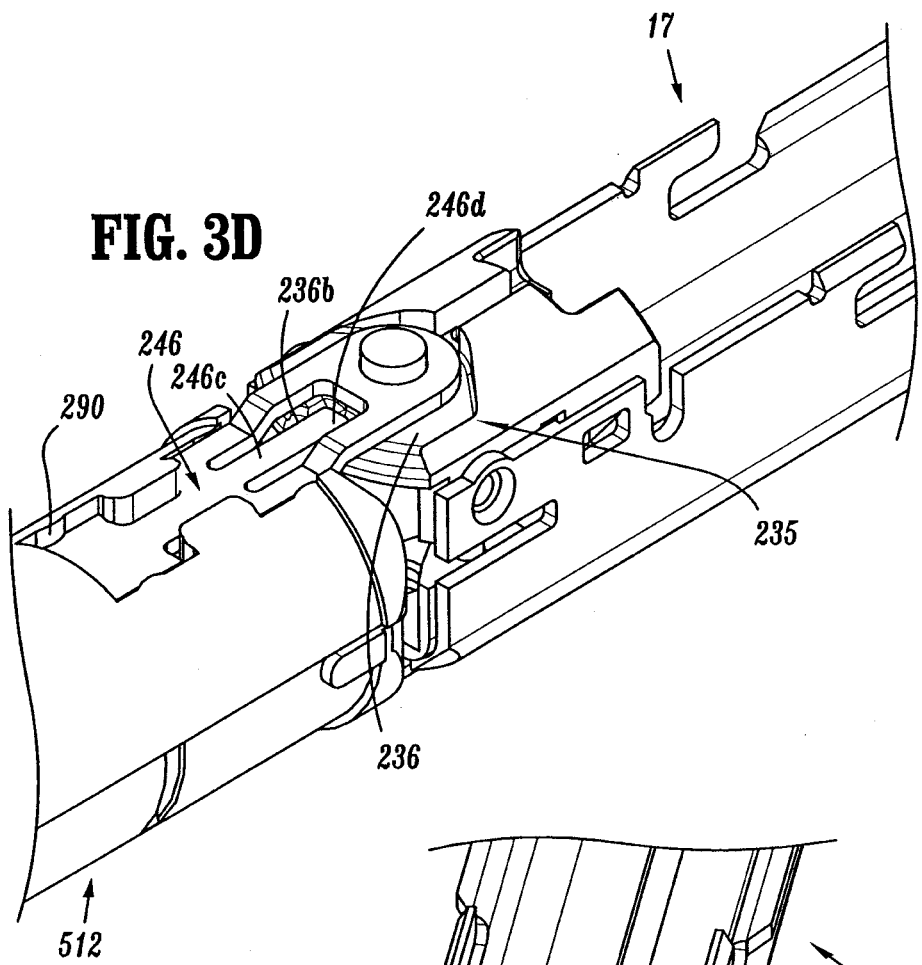
FIG. 3D is a side perspective view from above the proximal body portion, the mounting assembly and the tool assembly of the loading unit of the surgical instrument with the tool assembly in its non-articulated position.

Referring to FIGS. 3A-3C, each coupling member 246, 247 includes a cantilevered spring arm 246c which has a distal end 246d positioned to engage mounting assembly 235. More specifically, upper mounting portion 236 includes a top surface 236a which includes a recess 236b dimensioned to receive distal end 246d of spring arm 246c of a respective coupling member 246. Lower mounting portion 238 includes a bottom surface 238a having a pair of raised surfaces 238b which define a recess 238c which is dimensioned to receive spring arm 247c of a respective coupling member 247. Alternatively, at least one recess may be formed in the proximal end of tool assembly 17.

Figure 3E:
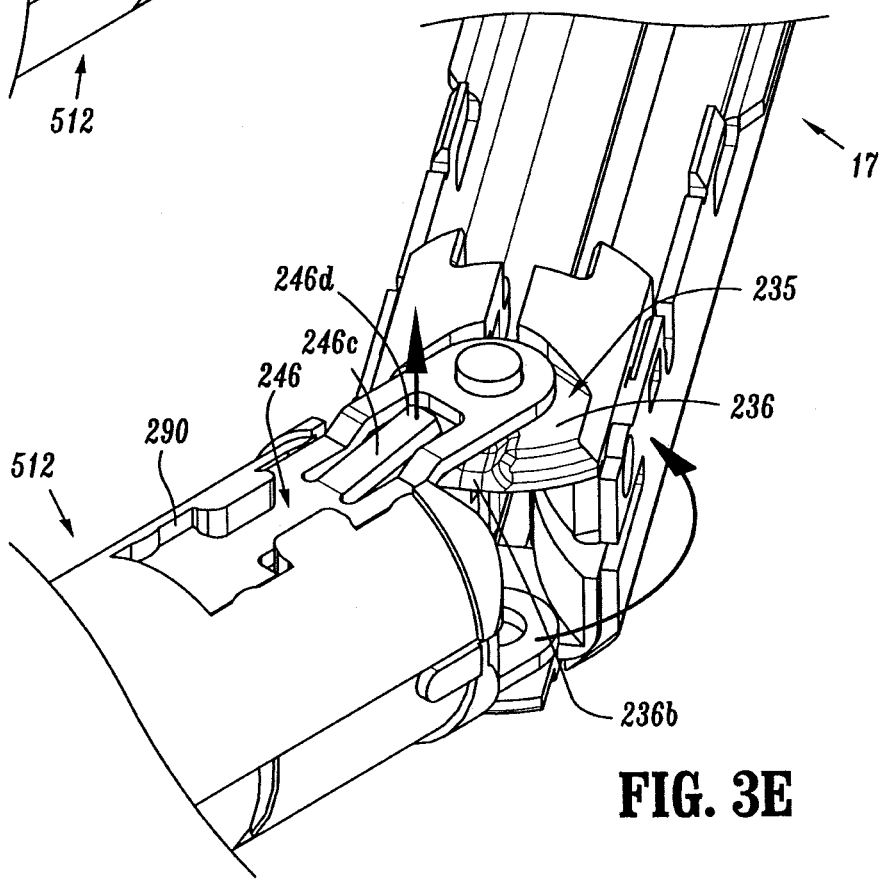
FIG. 3E is a side perspective view from above the proximal body portion, the mounting assembly and the tool assembly shown in FIG. 3D with the tool assembly in an articulated position.
Figure 3F:
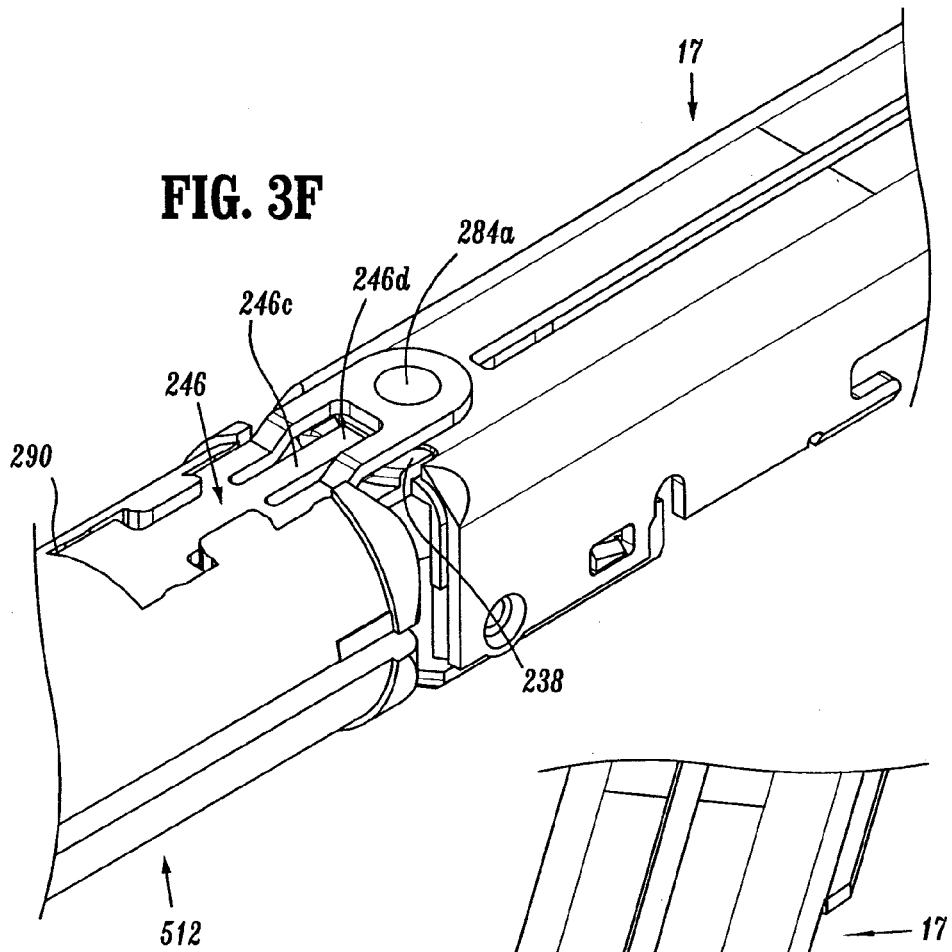
FIG. 3F is a side perspective view from below the proximal body portion, the mounting assembly and the tool assembly of the loading unit of the surgical instrument with the tool assembly in its non-articulated position.
Figure 3G:
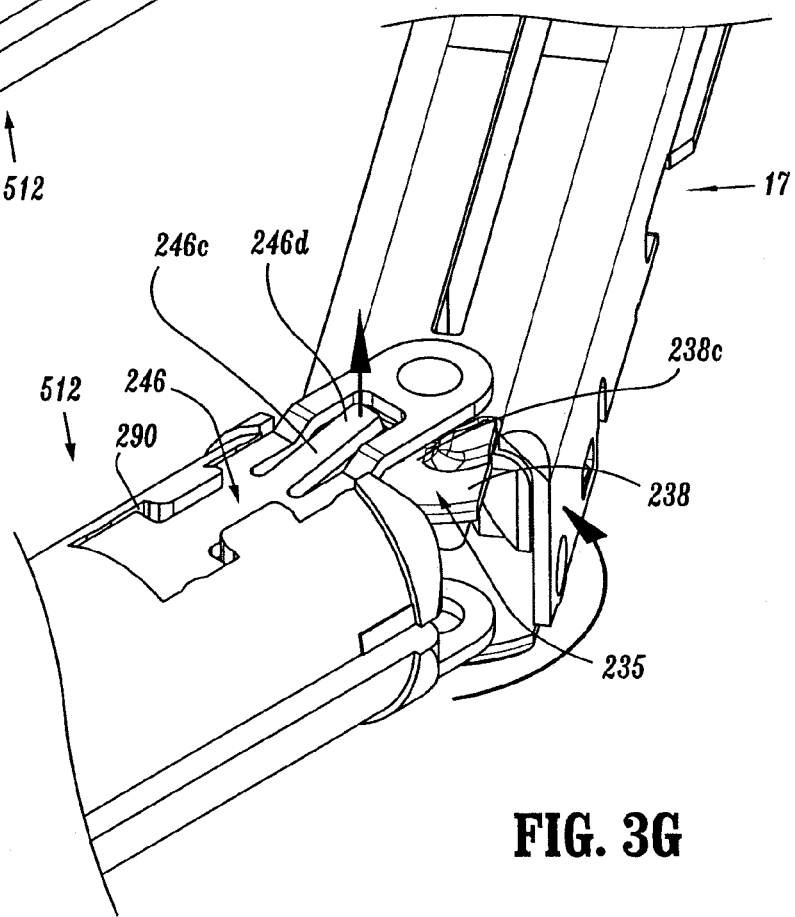
FIG. 3G is a side perspective view from below the proximal body portion, the mounting assembly and the tool assembly shown in FIG. 3F with the tool assembly in an articulated position.

As illustrated in FIGS. 3D-3G, when distal end of spring arms 246c, 247c of coupling members 246, 247 are positioned in recesses 236b and 238c of upper and lower mounting portions 236 and 238, respectively, spring arms 246c, 247c retain mounting assembly 235 in a non-articulated position. Spring arms 246c, 247c will retain mounting assembly 235 in its non-articulated position until a predetermined force sufficient to deflect spring arms 246c from recesses 236b and 238c is applied to effect articulation of mounting assembly 235 and tool assembly 17. When the predetermined force is applied to the mounting assembly 235 and tool assembly 17, spring arms 246c, 247c will spring or deflect outwardly from recesses 236b and 238c, as shown in FIGS. 3E and 3G, to permit pivotal movement of mounting assembly 235 (and, thus, tool assembly 17) in relation to the distal end of proximal body portion 200 of the loading unit 16.

As discussed above, spring arms 246c and recesses 236b and 238c maintain tool assembly 17 in its non-articulated position until a predetermined force has been applied to mounting assembly 235 to disengage spring arms 246c, 247c from recesses 236b and 238c of mounting assembly 235. It is envisioned that the spring aims/recesses could be incorporated into any articulating surgical device including staplers, graspers (See FIG. 3H), powered sealing devices, e.g., RF sealing devices, etc. Further, although two spring arms/recesses are shown, a single spring arm can be provided. Moreover, the articulating tool assembly need not form part of a loading unit but rather can be supported directly on the distal end of a surgical instrument. For example, the mounting assembly can be removably or irremovably secured to the tool assembly and secured directly to the distal end of a surgical instrument.

Upper housing half 250 and lower housing half 252 are contained within an outer sleeve 251 of body portion 200 (FIG. 3). Body portion 200 includes a cutout 251a dimensioned to receive a boss or projection 250a formed on upper housing half 250. The positioning of projection 250a within cutout 251a prevents axial and rotational movement of upper and lower housing halves 250 and 252 within outer sleeve 251 of body portion 200. In one embodiment, boss 250a has a substantially rectangular configuration having a greater axial dimension than lateral dimension. The greater axial dimension provides increased surface area for preventing rotation of upper and lower housing halves 250 and 252 within sleeve 251. A proximal portion 250b of boss 250a is ramped. Ramped proximal portion 250b allows sleeve 251 to be slid over boss 250a as upper and lower housing halves 250 and 252 are positioned within sleeve 251. It is envisioned that boss 250a may assume other configurations, e.g., circular, square, triangular, etc., and still achieve its intended function. Further, boss 250a can be repositioned anywhere along upper housing half 250 or, in the alternative, be positioned on lower housing half 252 or partly on each housing half 250 and 252.

The proximal end or insertion tip 193 of upper housing half 250 includes engagement nubs 254 for releasably engaging the distal end of a surgical instrument in a bayonet-type fashion (see FIGS. 1A and 7). Housing halves 250 and 252 define a channel 400 for slidably receiving axial drive assembly 212 therein. An articulation link 256 is dimensioned to be slidably positioned within a slot 402 formed between upper and lower housing halves 250 and 252. A pair of H-block assemblies 255 are positioned adjacent the distal end of housing portion 200 and adjacent the distal end of axial drive assembly 212 to prevent outward buckling and bulging of drive assembly 212 during articulation and firing of surgical instrument 10. Each H-block assembly 255 includes a flexible body 255a which includes a proximal end fixedly secured to body portion 200 and a distal end fixedly secured to mounting assembly 235 (FIG. 3).

A retention member 288 is supported on engagement section 270 of axial drive assembly 212. Retention member 288 includes a pair of fingers 288a which are releasably positioned within slots or recesses 252a formed in lower housing half 252. In operation, when loading unit 16 is attached to a surgical instrument and axial drive assembly 212 is actuated by applying a predetermined force to an actuation member 516 of the surgical instrument 500 (FIG. 11), axial drive assembly 212 is advanced distally to move drive assembly 212 and retention member 288 distally. As retention member 288 is advanced distally, fingers 288a are forced from recesses 252a to provide an audible and tactile indication that the surgical instrument has been actuated. Retention member 288 is designed to prevent inadvertent partial actuation of loading unit 16, such as during shipping, by maintaining axial drive assembly 212 at a fixed position within loading unit 16 until a predetermined axial force has been applied to axial drive assembly 212.

Axial drive assembly 212 includes an elongated drive beam 266 including a distal working head 268 and a proximal engagement section 270. In one embodiment, drive beam 266 is constructed from multiple stacked sheets of material. Engagement section 270 includes a pair of resilient engagement fingers 270a and 270b which mountingly engage a pair of corresponding retention slots formed in drive member 272. Drive member 272 includes a proximal porthole 274 configured to receive distal end of a control rod 520 (FIG. 11) of a surgical instrument when the proximal end of loading unit 16 is engaged with the body portion 512 of a surgical instrument 500.

Referring also to FIGS. 5-10, loading unit 16 further includes a locking mechanism including a locking member 300 and a locking member actuator 302. Locking member 300 (FIG. 6) is rotatably supported within a longitudinal or axial slot 310 (FIG. 7) formed in a proximal portion of upper housing half 250 of body portion 200 of loading unit 16. Locking member 300 is movable from a first position (FIGS. 7 and 8), in which locking member 300 maintains drive assembly 212 in a prefired position, to a second position (FIGS. 9 and 10), in which drive assembly 212 is free to move axially.

Figure 6:
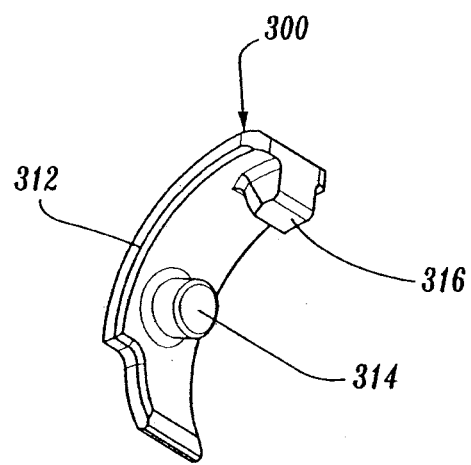
FIG. 6 is a bottom perspective view of a locking member of the locking mechanism shown in FIG. 3.
Figure 10:
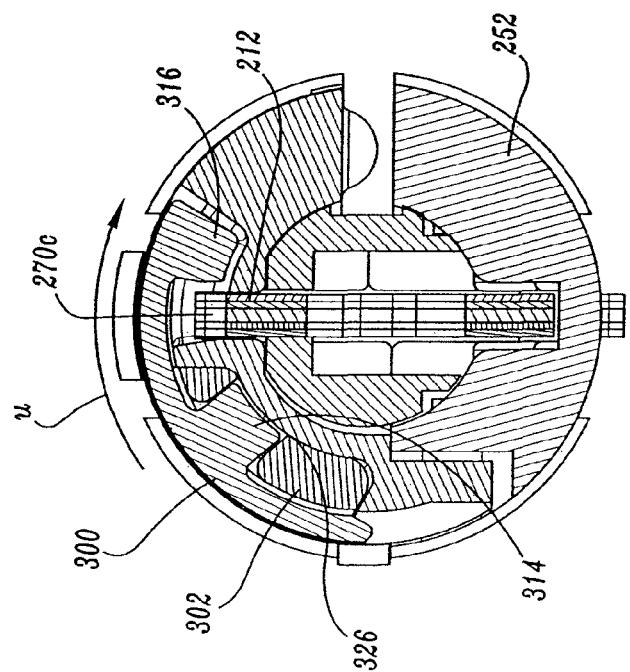
FIG. 10 is a cross-sectional view taken along section lines 10-10 of FIG. 9.
Figure 9:
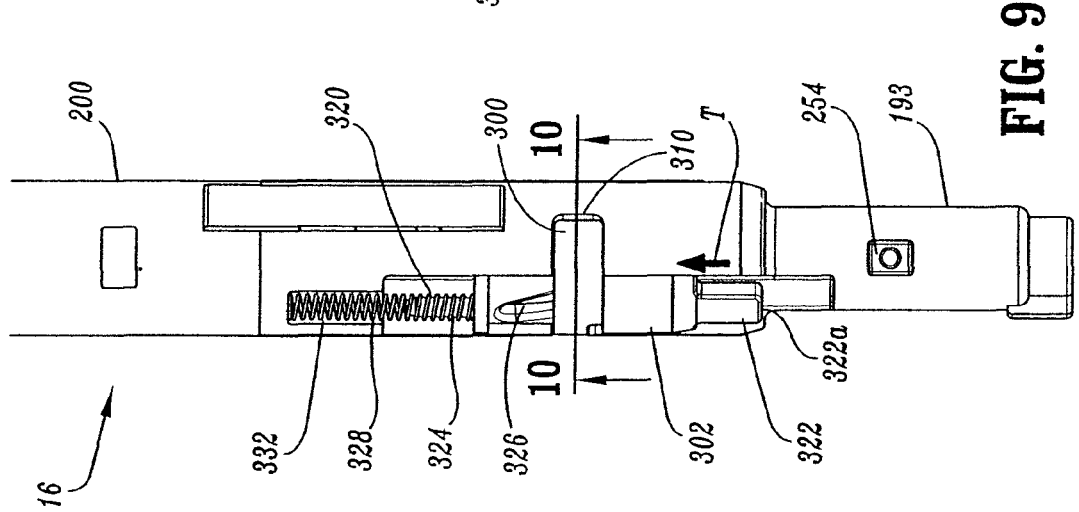
FIG. 9 is a top view of the proximal end of the loading unit proximal body portion shown in FIG. 1A with the locking mechanism in its unlocked position.

As illustrated in FIG. 6, locking member 300 includes semi-cylindrical body 312 which is slidably positioned within transverse slot 310 formed in upper housing half 250 of body portion 200. Body 312 includes a radially inwardly extending cam member 314 and a radially inwardly extending finger 316. Finger 316 is dimensioned to be slidably received within a notch or slot 270c (FIG. 3) formed in drive assembly 212. Engagement of finger 316 in notch 270c of drive assembly 212 prevents drive assembly 212 from moving linearly within body portion 200 and, thus, prevents actuation of loading unit 16.

Figure 5:
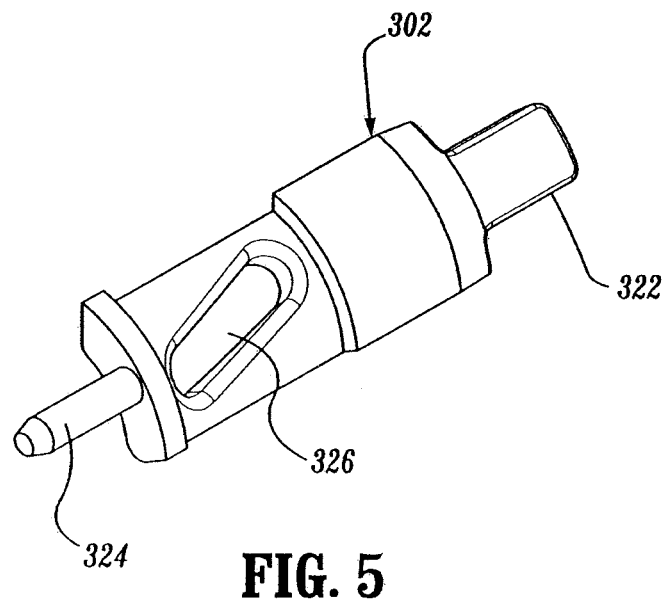
FIG. 5 is a top perspective view of the lock member actuator of the proximal body portion locking mechanism shown in FIG. 3.

Referring to FIGS. 3, 5 and 7, a locking member actuator 302 is slidably positioned within a axial slot 320 (FIG. 7) formed in upper housing half 250 of body portion 200 of loading unit 16. Actuator 302 includes a proximal abutment member 322, a distal spring guide 324, and a central cam slot 326. Axial slot 320 intersects transverse slot 310 such that cam member 314 of locking member 300 is slidably positioned within cam slot 326 of locking member actuator 302. A biasing member or spring 328 (FIG. 7) is positioned about spring guide 324 between a distal surface 330 of actuator 302 and a wall 332 (FIG. 7) defining the distal end of axial slot 320. Spring 328 urges actuator 302 to its retracted position within axial slot 320. In its retracted position, abutment member 322 is positioned on and extends radially outwardly of the proximal end of loading unit 16 adjacent insertion tip 193 of proximal body portion 200 and cam slot 326 is positioned to locate cam member 314 such that finger 316 of lock member 300 is positioned within notch 270c of drive assembly 212.

FIGS. 11-15 illustrate loading unit 16 and surgical instrument 500 prior to and during attachment of loading unit 16 to surgical instrument 500. Prior to attachment of loading unit 16 onto surgical instrument 500, spring 328 urges actuator 302 to its retracted position to move lock member 300 to its locked position as discussed above. When insertion tip 193 loading unit 16 is linearly inserted into the open end 522 (FIG. 11) of the body portion 512 (FIG. 13) of a surgical instrument 500, nubs 254 move linearly through slots (not shown) formed in open end 522 of body portion 512. As nubs 254 pass through the slots, the proximal end 322a of abutment member 322, which is angularly offset from nubs 254, abuts a wall 276c defining the slots for receiving nubs 254. As loading unit 16 is moved further into body portion 512, locking member actuator 302 is moved from its retracted position to its advanced position in the direction indicated by arrow "T" in FIG. 14. As actuator 302 is moved to its advanced position, lock member 300 is cammed in the direction indicated by arrow "U" in FIG. 14 from its locked position (FIG. 8) engaged with drive assembly 212 to its unlocked position (FIG. 10) to move finger 316 from notch 270c. The locking mechanism including locking member 300 and locking member actuator 302 prevents accidental or inadvertent advancement or manipulation of the drive member of loading unit 16 such as during loading of loading unit 16 onto a surgical instrument 500.

When loading unit 16 has been moved linearly in relation to instrument 500 to a position wherein a proximal surface 530 of body portion 200 abuts inner surface 276c of body portion 512 (FIG. 15), loading unit 16 can be rotated in relation to body portion 512 in a bayonet-type action to position nubs 254 within openings 536 of body portion 512 to lock loading unit 16 onto body portion 512. It is envisioned that other coupling types besides bayonet couplings may be used to connect loading unit 16 to instrument 500, e.g., spring detent or snap-fit couplings, friction fit couplings, interlocking members, threaded couplings etc.

In an embodiment of the present disclosure illustrated in FIGS. 16-20, a locking assembly 600 is illustrated for use with surgical instrument 500 and disposable loading unit 16 (see FIG. 1, for example). In the illustrated embodiments, locking assembly 600 includes a housing 602, a pusher 604, a rod 606, a slide 608, at least one spring 610, a cam finger 612, a pivot plate 614 having slots 616 and a link 618. Locking assembly 600 generally helps tool assembly 17 (see FIG. 1, for example) maintain its position during firing of surgical instrument 500.

Figure 16:
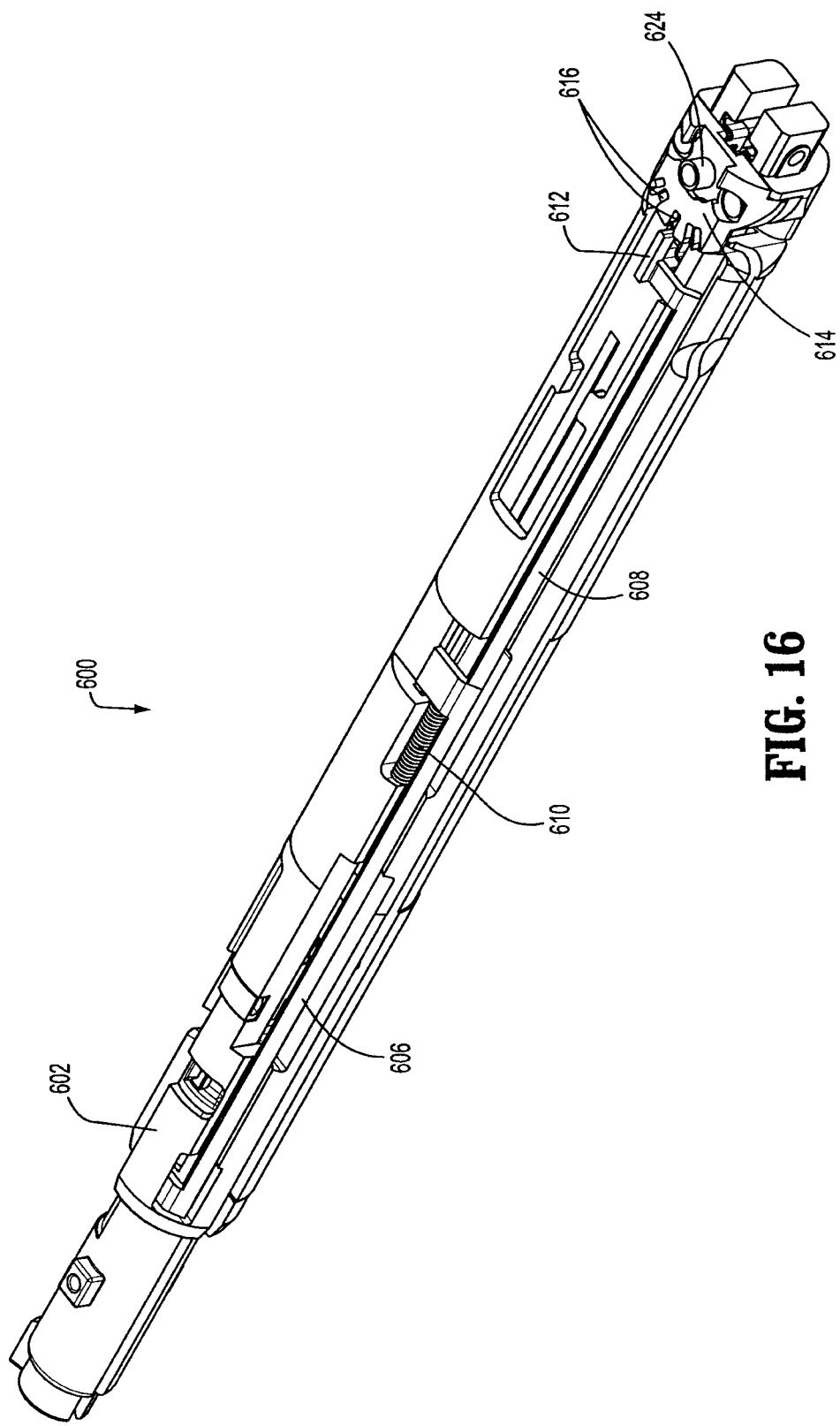
FIG. 16 is a perspective view of a locking assembly for use with a surgical instrument in accordance with an embodiment of the present disclosure.
Figure 17:
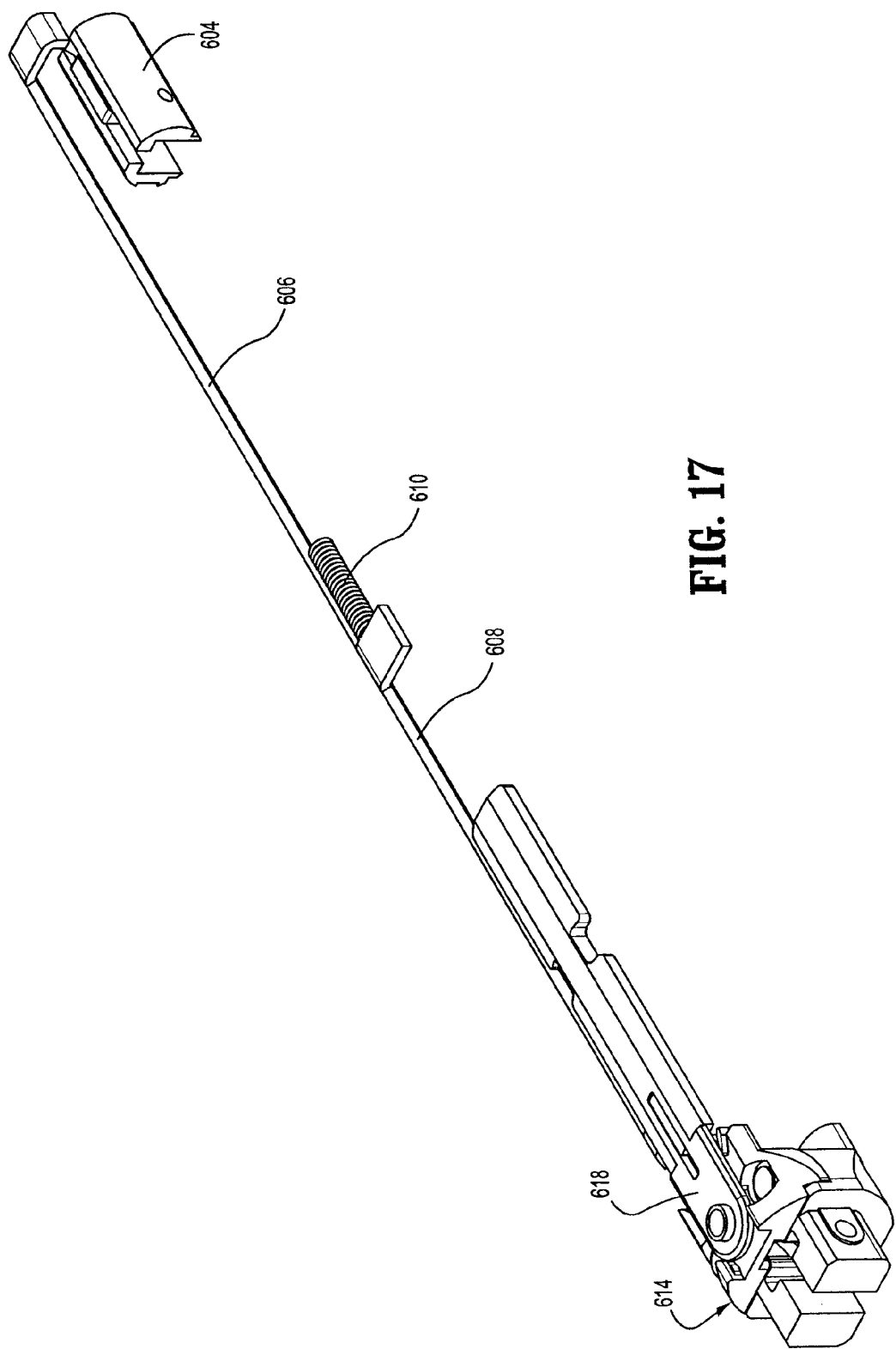
FIG. 17 is a perspective view of various components of the locking assembly of FIG. 16.

Referring to FIGS. 16 and 17, a portion of locking assembly 600 is at least partially contained within a housing 602. FIG. 16 illustrates locking assembly 600 disposed in relation to housing 602, while FIG. 17 illustrates locking assembly 600 isolated from housing 602. In the illustrated embodiment of FIG. 17, pusher 604 is shown with rod 606 extending distally therefrom. Slide 608 extends distally from rod 606 and is in a slidable relationship therewith, thus allowing slide 608 to move axially with respect to rod 606. Spring 610 or pair of springs (not explicitly shown in this embodiment) distally biases slide 608 from rod 606.

Figure 18:
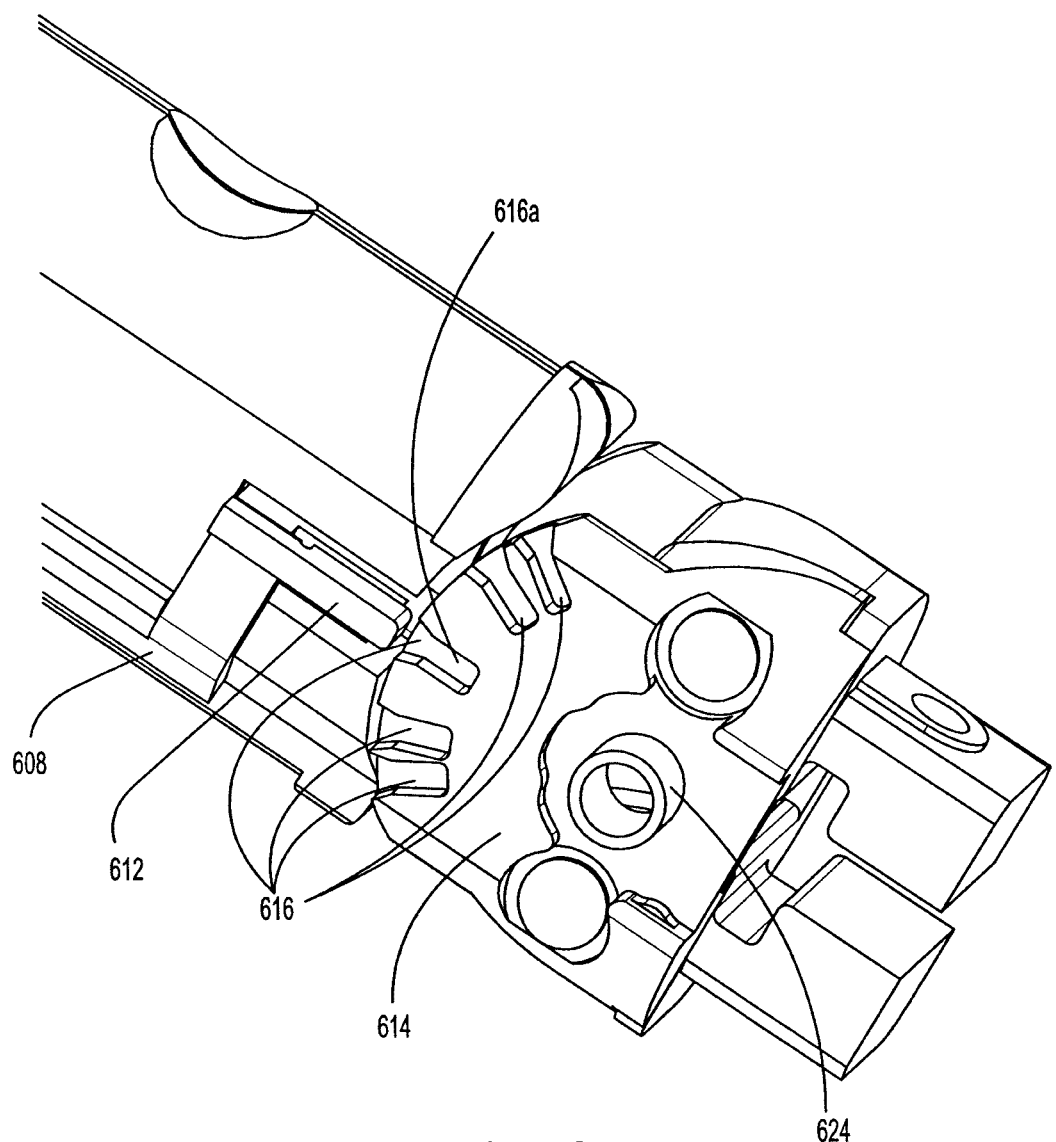
FIG. 18 is an enlarged perspective view of a portion of the locking assembly of FIGS. 16 and 17 illustrated with the articulating tool assembly in a non-articulated position.
Figure 19:
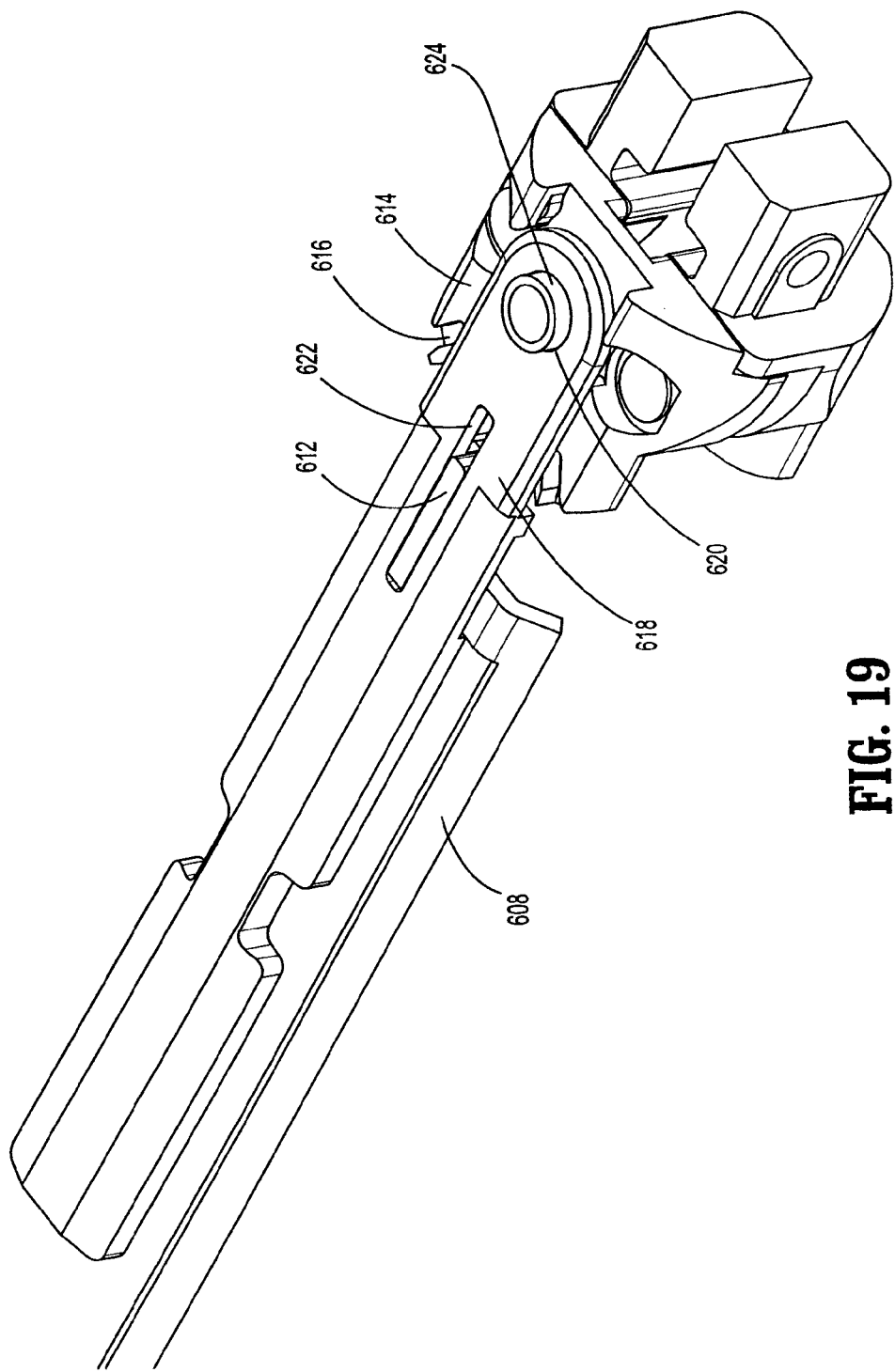
FIG. 19 is an enlarged perspective view of a portion of the locking assembly of FIGS. 16-18 and including a link.
Figure 20:
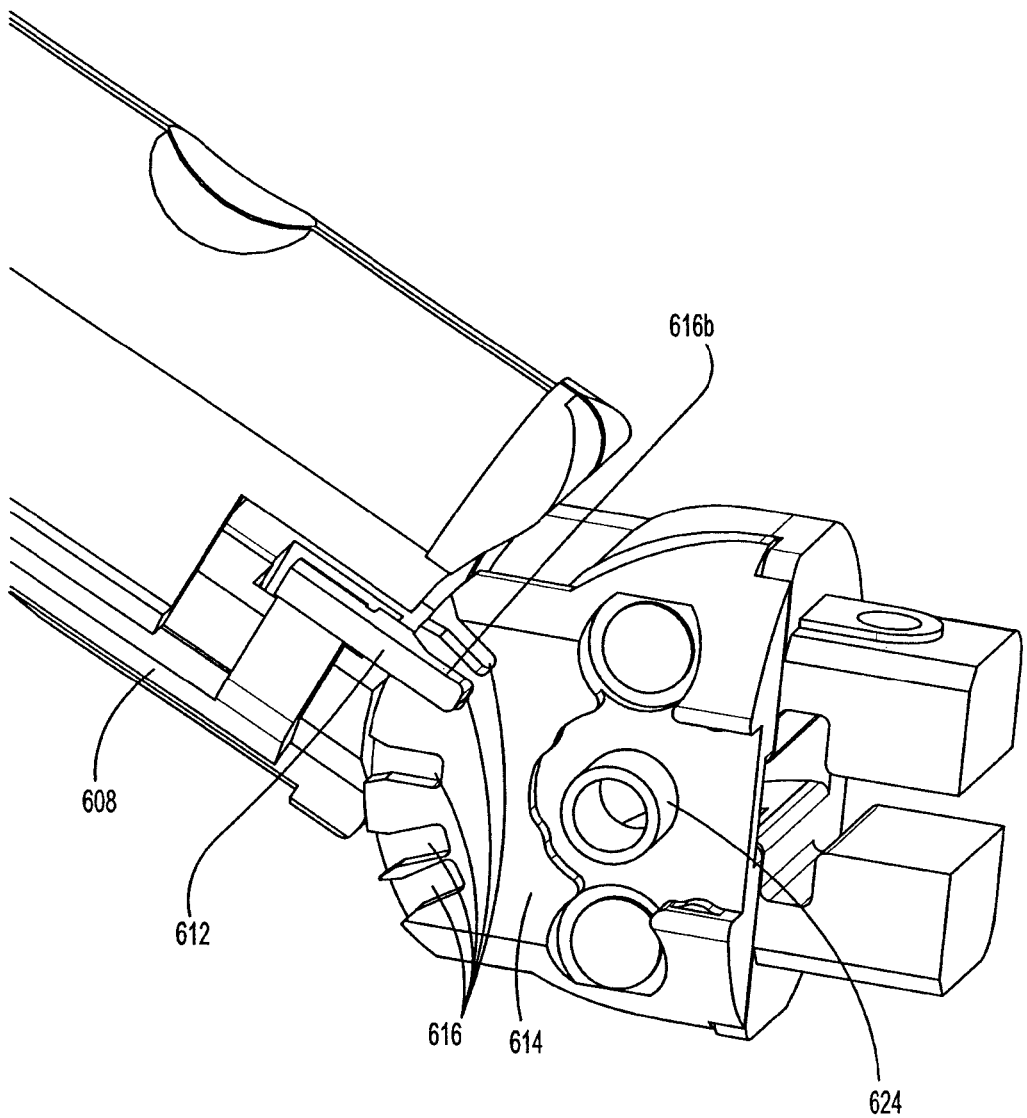
FIG. 20 is an enlarged perspective view of a portion of the locking assembly of FIGS. 16-19 illustrated with the articulating tool assembly in an articulated position.

Now referring to FIGS. 18-20, cam finger 612 and pivot plate 614 are illustrated. Cam finger 612 extends distally from slide 608 and pivot plate 614 may be disposed on mounting assembly 235 (see FIG. 3), for example. It is envisioned that pivot plate 614 may be disposed on or incorporated with a portion of tool assembly 17. A plurality of slots 616 (five slots 616 are illustrated) is disposed on pivot plate 614 and are sized to accept at least a portion of cam finger 612 therein. Upon different amounts of articulation of tool assembly 17 (including no substantial articulation) with respect to body portion 512 (see FIG. 1, for example), cam finger 612 is approximately aligned with an individual slot 616 of pivot plate 614. FIGS. 18 and 19 illustrate cam finger 612 substantially aligned with a center slot 616a (hidden from view in FIG. 19) and FIG. 20 illustrates cam finger 612 substantially aligned with a side slot 616b.

Link 618, illustrated in FIGS. 17 and 19, is in mechanical engagement with pivot plate 614 and cam finger 612. (In FIG. 18, the link has been removed.) Link 618 is illustrated having an opening 620 and a slot 622 (FIG. 19). Opening 620 is in a pivotal relationship with a boss 624 on pivot plate 614 and slot 622 is slidably engaged with cam finger 612. This relationship allows for articulation of pivot plate 614 with respect to body portion 512 and for longitudinal translation of slide 608 with respect to pivot plate 614.

In operation, upon at least a partial actuation of movable handle 516 (see FIG. 1, for example), pusher 604 is forced distally, e.g., via control rod 520 (see FIG. 11, for example), thus causing distal translation of cam finger 612 at least partially into a slot 616 of pivot plate 614. It is envisioned that actuating movable handle 516 to approximate cartridge assembly 18 and an anvil assembly 20 (see FIG. 1A, for example) also functions to translate cam finger 612 distally. In such an embodiment, when articulating tool assembly 17 is in place and clamped on tissue, further articulation cannot be accomplished (without releasing movable handle 516, for example). Thus, locking assembly 600 helps maintain articulating tool assembly 17 in position with respect to body portion 512, prior to emplacing staples into tissue, for example.

As discussed above, spring 610 distally biases slide 608 from rod 606. This biasing provided by spring 610 helps ensure cam finger 612 is not accidentally or prematurely dislodged from slot 616 of pivot plate 614, which may result in a significant amount of "play" therebetween. Additionally, the distal bias provided by spring 610 helps eliminate manufacturing tolerances and/or clearances that are present between slide 608 and pivot plate 614. It is also envisioned that at least a portion of cam finger 612 and/or slot 616 may be wedge-shaped to help reduce any unintended movement therebetween. In such an embodiment, a distal portion of cam finger 612 and slot 616 would be narrower than a corresponding proximal portion.

Figure 21:
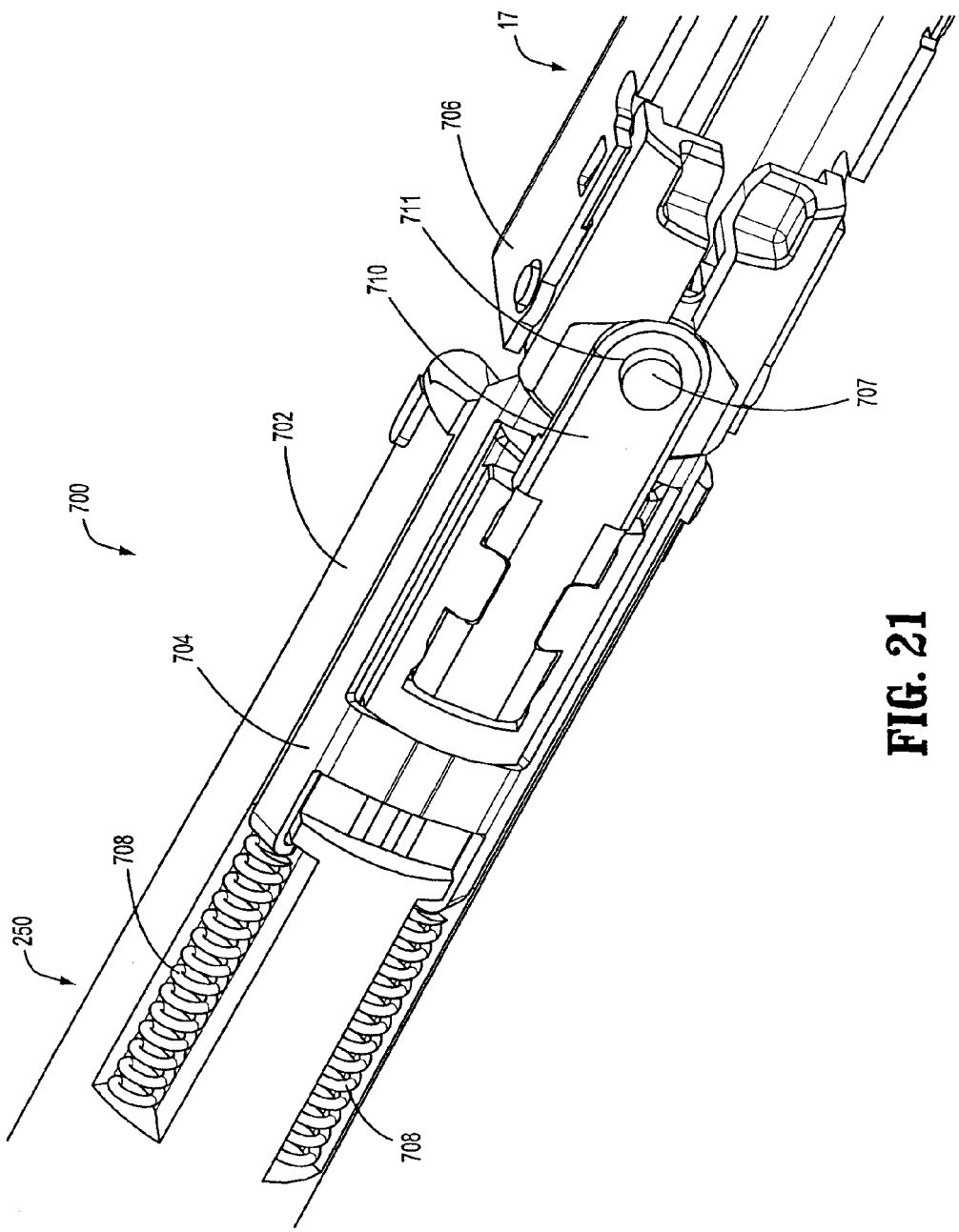
FIG. 21 is an enlarged perspective view of another locking assembly for use with a surgical instrument in accordance with an embodiment of the present disclosure.
Figure 22:
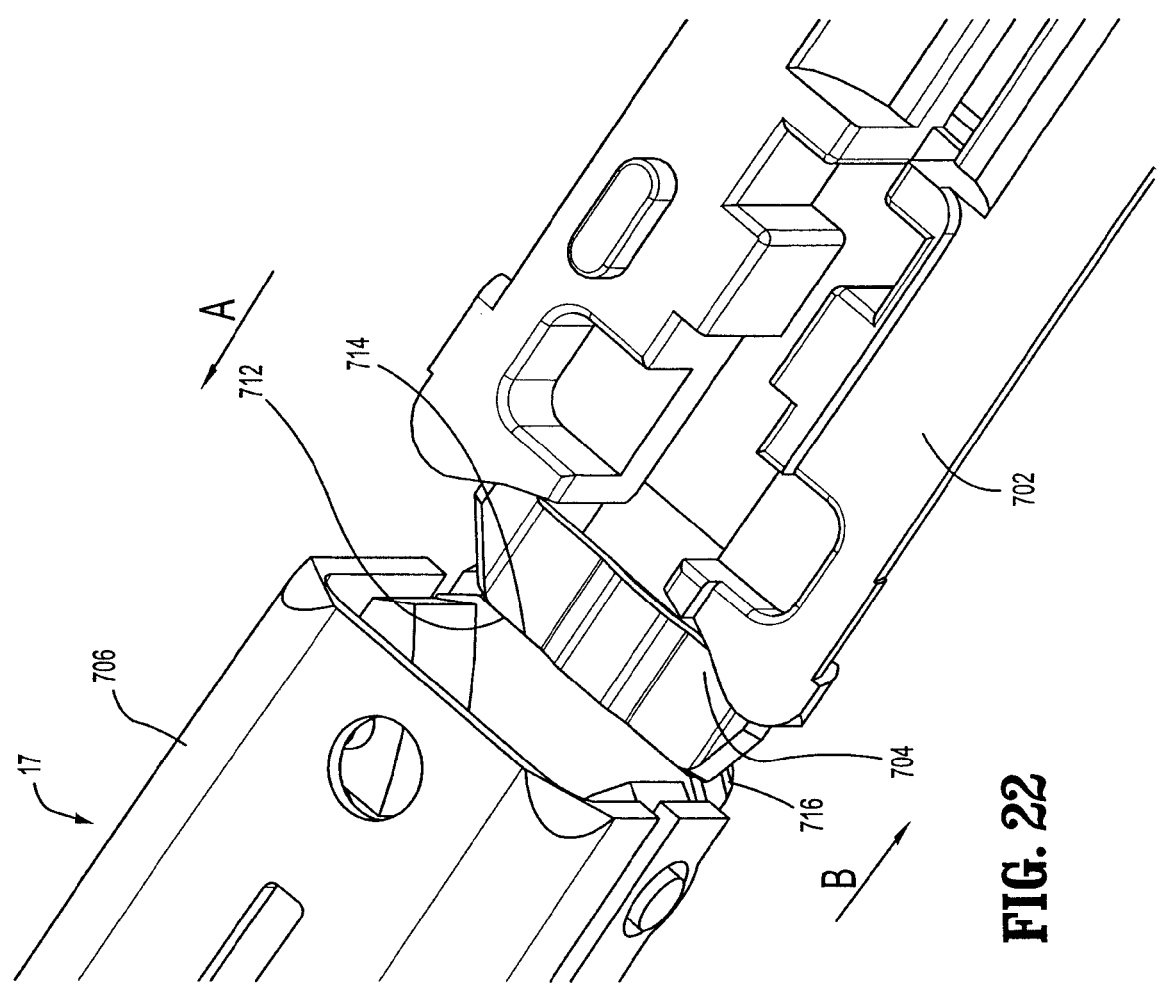
FIG. 22 is an enlarged bottom perspective view of the locking assembly of FIG. 21.

In an embodiment of the present disclosure illustrated in FIGS. 21 and 22, a locking assembly 700 is illustrated for use with surgical instrument 500 and disposable loading unit 16 (see FIG. 1, for example). In the illustrated embodiment, locking assembly 700 includes an adapter 702, a pusher 704, a pivot 706, a biasing element (e.g., a pair of springs 708) and a link 710. Locking assembly 700 generally helps maintain tool assembly 17 in a predetermined position.

With reference to FIG. 21, adapter 702 of locking assembly 700 is generally housed within body portion 512 (see FIG. 1, for example) of surgical instrument 500 or within disposable loading unit 16. In the illustrated embodiment, pusher 704 is located distally of a pair of springs 708. Pusher 704 is distally biased via the pair of springs 708 towards pivot 706 of articulating tool assembly 17. A distal portion of pusher 704 includes a pusher mating surface 712 (FIG. 22) which is shaped and dimensioned to mate with a pivot mating surface 714 (FIG. 22) disposed adjacent a proximal portion of pivot 706. Link 710 is illustrated in mechanical cooperation with a portion of pusher 704 and pivotably connected to a portion of pivot 706, thus allowing articulating tool assembly 17 to move between its first position and its second position with respect to body portion 512. More specifically, link 710 includes an opening 711 that fits over a protrusion 707 of pivot 706, thus allowing pivotal movement therebetween. Further, link 710 is slidably engaged with a portion of adapter 702, thus allowing longitudinal movement therebetween.

Now referring to FIG. 22, pusher mating surface 712 is substantially flat along a majority of its length in this embodiment. Correspondingly, pivot mating surface 714 is also flat along a majority of its length in the illustrated embodiment. Thus, the distal bias of pusher 704 towards pivot 706 (in the direction of arrow A) via the pair of springs 708, helps maintain articulating tool assembly 17 in its first, non-articulated, position, as the biasing force helps articulating tool assembly 17 resist pivoting. While two springs 708 are illustrated, more or fewer springs 708 may be provided.

To pivot articulating tool 17 from its first, non-articulated position, the distal biasing force from pair of springs 708 must be overcome. Such a pivoting action, moves pusher 704 proximally (in the direction of arrow B) against the bias of pair of springs 708. It is also envisioned that pusher mating surface 714 includes detents (not explicitly shown in this embodiment) to help stabilize articulating jaw member 17 in selected articulated positions.

With continued reference to FIG. 22, pivot 706 includes a shelf 716 thereon. As shown in FIG. 22, shelf 716 overlaps at least a portion of pusher 704 when pusher mating surface 712 is in contact with pivot mating surface 714. Shelf 716 is situated and configured to help prevent tissue from being pinched between pusher 704 and pivot 706 when articulating tool assembly 17 is rotated and/or articulated.

Figure 23:
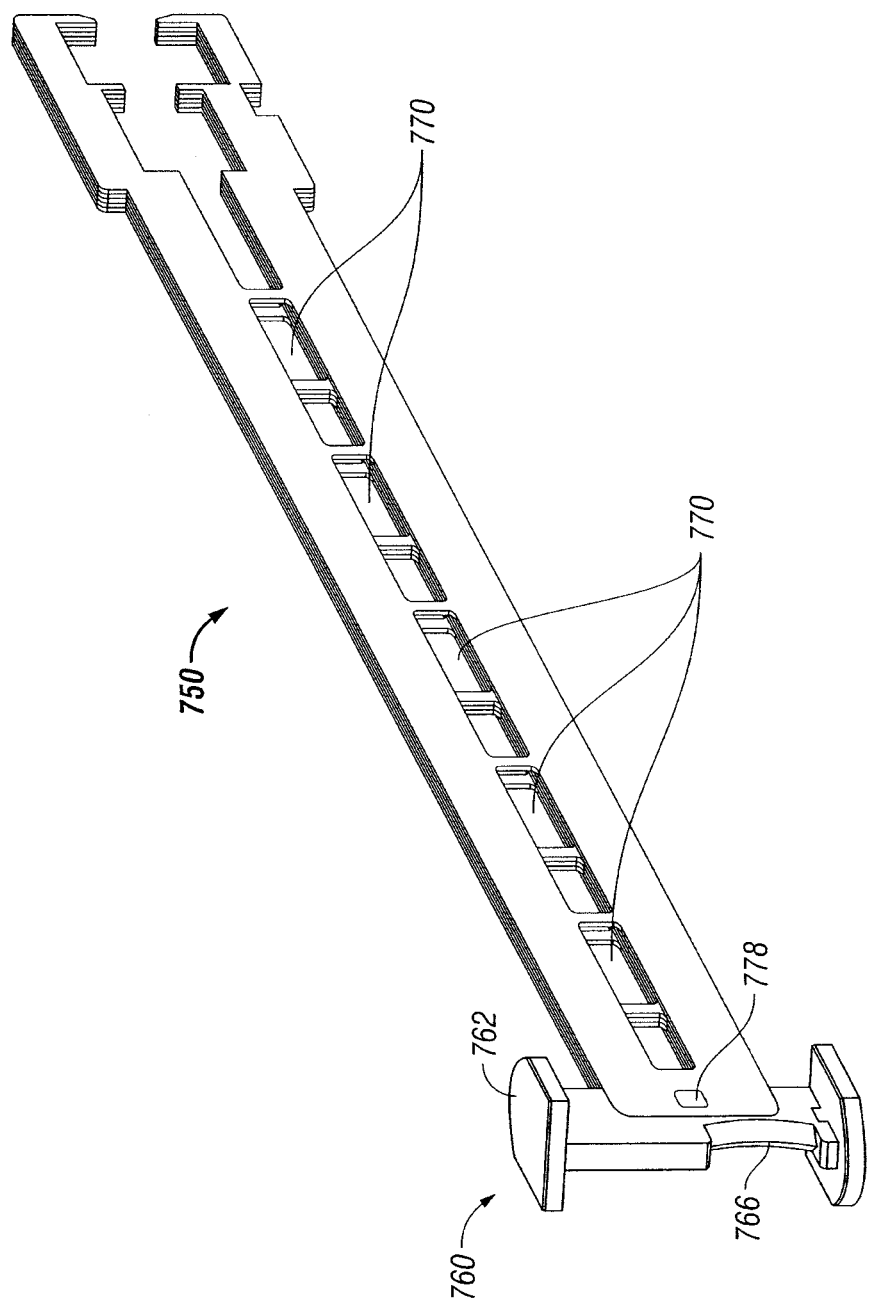
FIG. 23 is a perspective view of a drive beam having a plurality of layers and a closure apparatus in accordance with an embodiment of the present disclosure.
Figure 24:
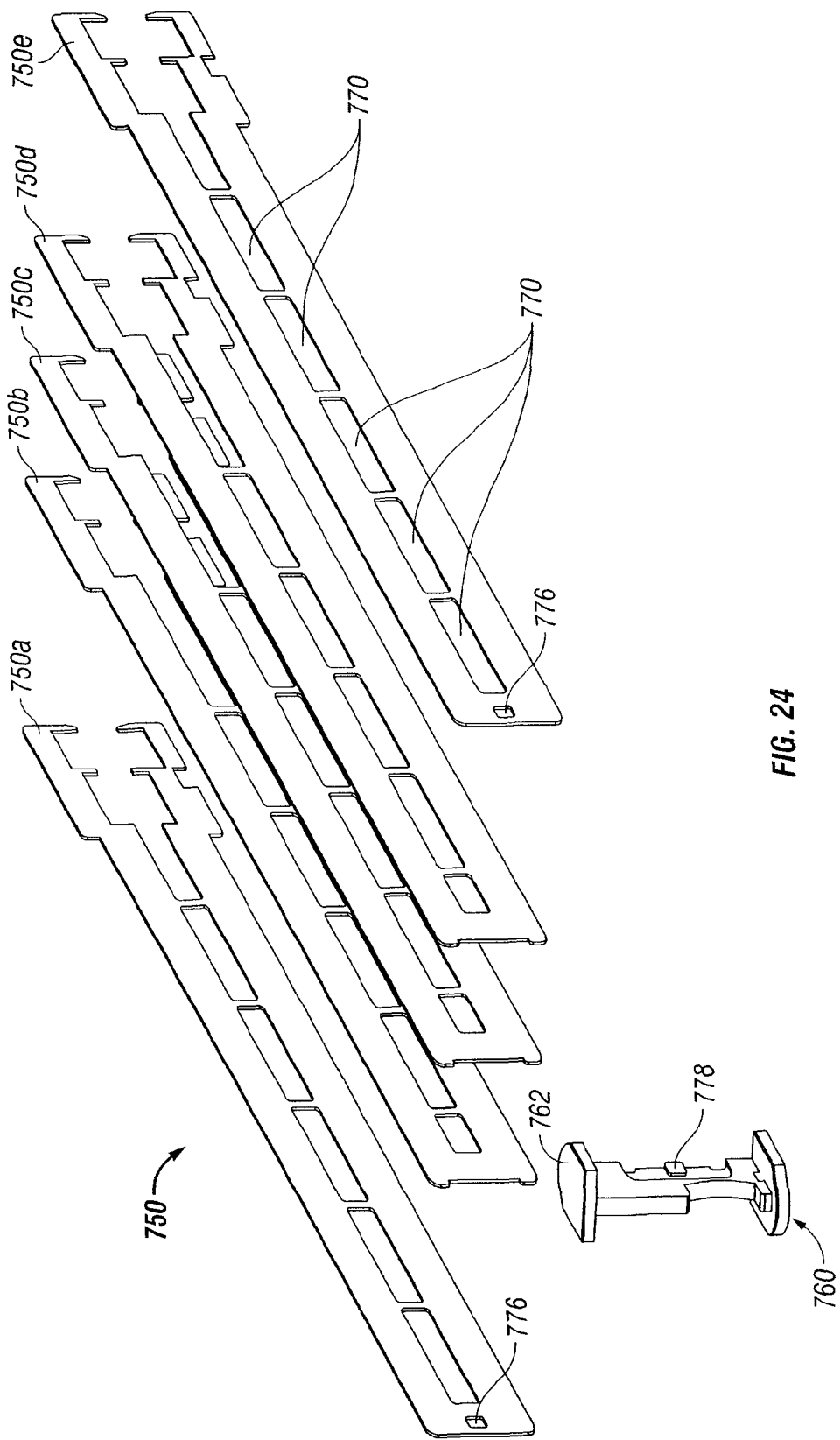
FIG. 24 is a perspective view of the drive beam and closure apparatus of FIG. 23 with parts separated.
Figure 25:
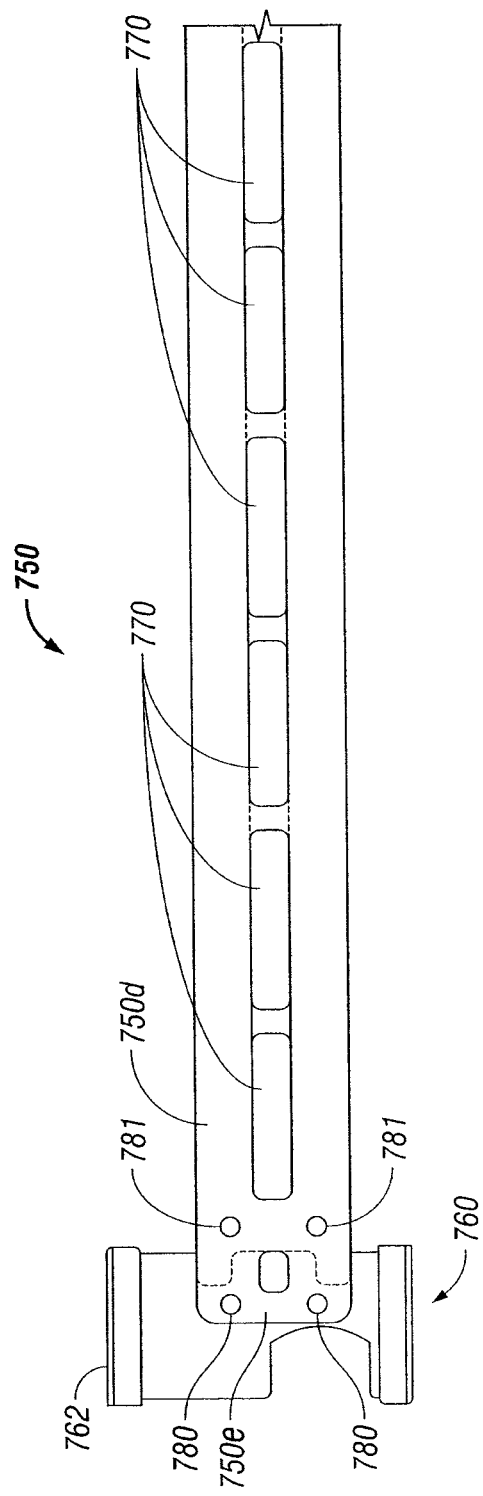
FIG. 25 is a cross-sectional view of a portion of the drive beam and closure apparatus of FIGS. 23 and 24.

In an embodiment of the present disclosure illustrated in FIGS. 23-25, a multi-layered drive beam 750 having a plurality of layers 750a-750e is illustrated and may be included in a disposable loading unit 16 (see FIG. 1, for example). A closure apparatus 760, such as an I-beam, is also illustrated. Closure apparatus 760 includes a horizontal portion 762 that is advanceable into camming surface 42 (or other contact surface) to approximate tool assembly tool assembly 17, as described in detail above with reference to FIG. 2.

With reference to FIG. 24, multi-layered drive beam 750 having five layers 750a-750e is illustrated. It is envisioned and within the scope of the present disclosure that fewer or more layers may be used to form multi-layered drive beam 750. It is also envisioned that multi-layered drive beam 750 may replace drive beam 266 in other embodiments of this disclosure. Use of multi-layered drive beam 750 may provide increased strength and flexibility during use, specifically, for instance, while tool assembly 17 is in an articulated position.

A plurality of cutouts 770 is illustrated in FIGS. 23-25 which extend through each layer of multi-layered drive beam 750. Although the figures show between five and ten cutouts per layer of multi-layered drive beam 750, the exact number of cutouts 770 may be fewer than five, between five and ten, or greater than ten. Additionally, cutouts 770 of adjacent layers of drive beam 750 may or not align with each other. The use of cutouts 770 reduces cross-sectional dimensions of drive beam 750 and allows for bending force adjustment. While rectangular cutouts 770 are illustrated, the use of cutouts 770 having other regular or non-regular shapes is also contemplated.

The attachment of each layer 750a-750e of multi-layered drive beam 750 and the attachment to closure apparatus 760 are illustrated in FIG. 25. In the illustrated embodiment, an outer layer (750a or 750e of FIG. 24) is affixed to closure apparatus 760 in two locations (each location being indicated by numeral 780 in FIG. 25), via a pair of spot welds, for example. It is also envisioned that each outer layer 750a, 750e includes an aperture 776 that fits over a boss 778 protruding from closure apparatus 760. Each outer layer 750a, 750e is also affixed to an adjacent layer (e.g., 750b or 750d) in two locations (each location being indicated by numeral 781 in FIG. 25), possibly via a pair of spot welds. Further, each inner layer (e.g., 750b, 750c and 750d) is attached to an adjacent inner layer (for instance, 750b is attached to 750c; 750c is attached to 750b and 750d; and 750d is attached to 750c) in two locations, via spot welds, for example. While spot welding is disclosed as an attachment method, other methods for attaching each layer to each other and the outer layers to the closure apparatus are envisioned and within the scope of the present disclosure. The illustrated embodiments show attachments points 780 of inner layers adjacent closure apparatus 760, but it is envisioned and within the scope of the present disclosure that attachment points 780 are disposed in other locations on drive beam 750. Additionally, it is envisioned that at least one layer of drive beam 750 is made of a metal, such as stainless steel. Portions of drive beam 750 and/or closure apparatus 760 may also be made of or at least partially coated with a plastic material, as described below. Further, closure apparatus 790 may include a cutting surface 766 (FIG. 23) thereon for cutting tissue.

Figure 26:
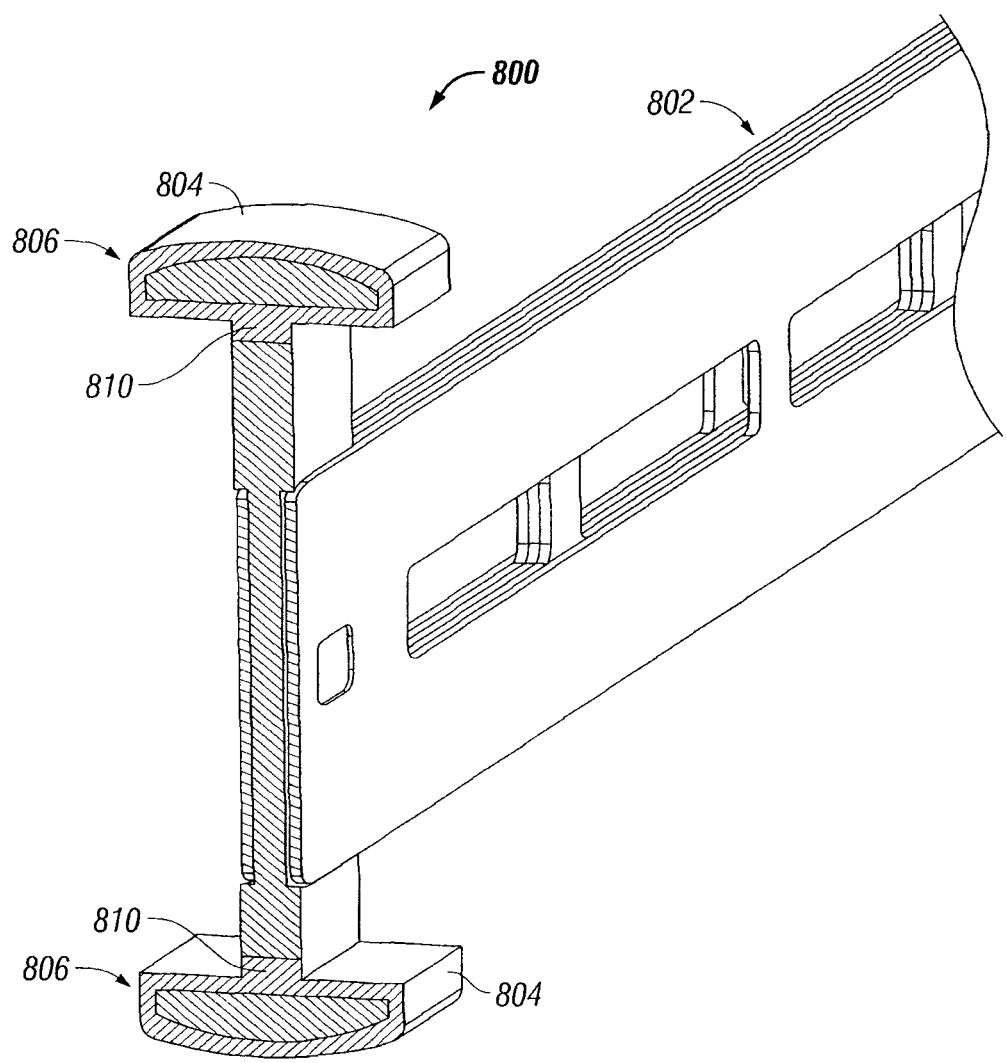
FIG. 26 is a partial cross-sectional view of a drive beam and a closure apparatus in accordance with an embodiment of the present disclosure.
Figure 27:
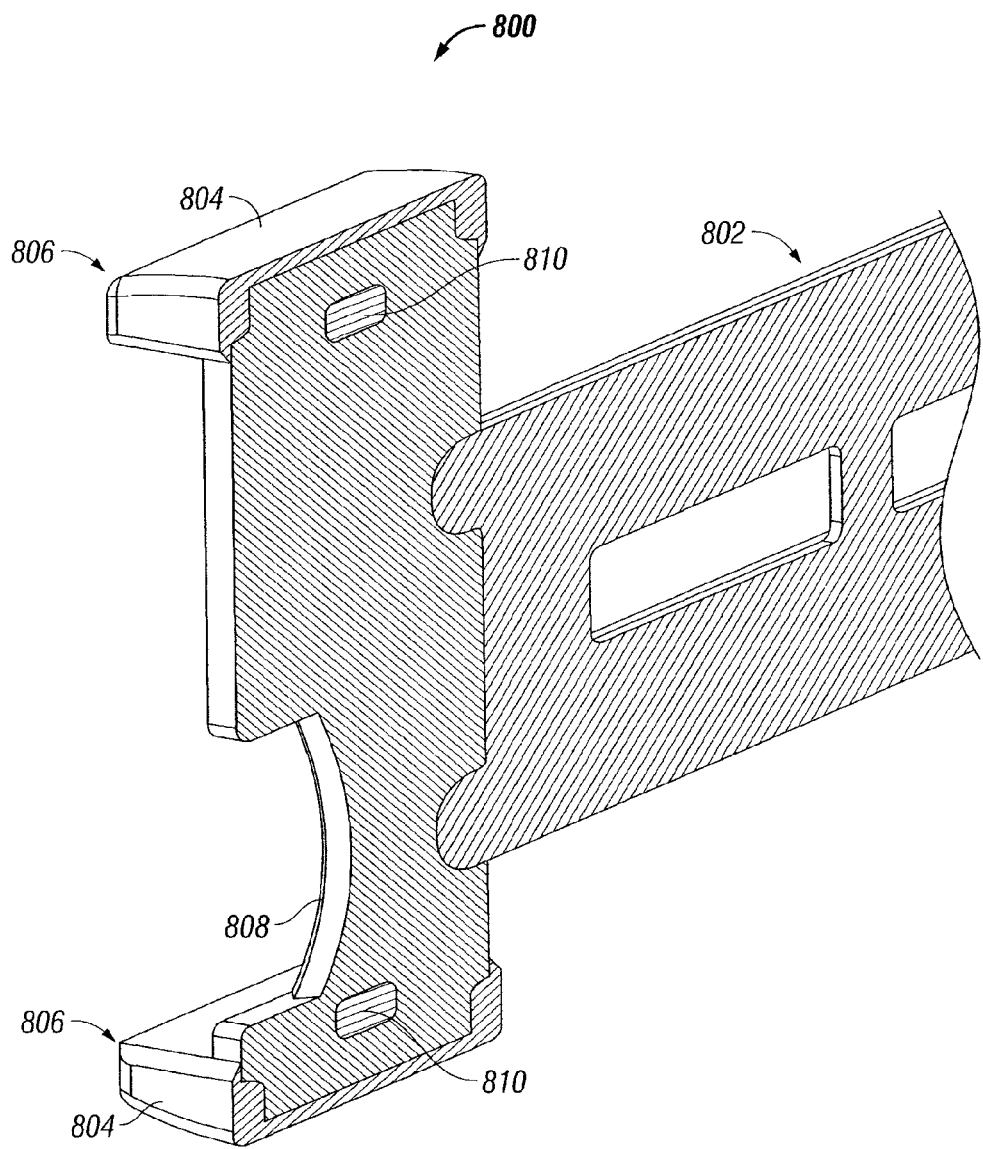
FIG. 27 is a cross-sectional view of the drive beam and closure apparatus of FIG. 26.

In an embodiment of the present disclosure illustrated in FIGS. 26 and 27, a closure apparatus 800 and a portion of drive beam 802 are shown. Closure apparatus and/or a contact surface (e.g., camming surface 42) of tool assembly 17 (see FIG. 2, for example) may include a plastic surface or plastic coating. In this embodiment, closure apparatus 800 is illustrated having a pair of caps 804 at least partially covering horizontal portions 806 of closure apparatus 800. Caps 804 may be made of plastic in this embodiment. Such plastic surfaces disposed on closure apparatus 800 and/or contact surface of tool assembly 17 generally reduce the amount of friction therebetween vis-à-vis two metal surfaces. That is, a plastic to metal or a plastic to plastic interaction may create less friction than interaction between a pair of metal surfaces. This reduced amount of friction may correspond to a reduced firing force.

It is envisioned that a portion of closure apparatus 800, such as pair of caps 804, is made of plastic, overmolded with plastic or includes a plastic coating. Additionally, a contact surface of tool assembly 17, or at least a portion thereof, may also be made of plastic, be overmolded with plastic or include a plastic coating.

In an embodiment of the disclosure, closure apparatus 800 may include an I-shaped cross section, as illustrated in FIGS. 26 and 27. Additionally, closure apparatus 800 and drive beam 802 may be part of a disposable loading unit 16 and/or part of a surgical instrument 500 that is able to articulate. Further, drive beam 802 may include a single layer or a plurality of layers (as shown in FIG. 26) and at least a portion of drive beam 802 may be made of plastic. Still further, closure apparatus 800 may include a cutting surface 808 (FIG. 27) thereon for cutting tissue.

With continued reference to FIGS. 26 and 27, plastic cap 804 may include a reinforced section 810 which may increase the strength of closure apparatus 800 or may provide a stronger connection between cap 804 and horizontal portion 806 of closure apparatus 800. It is also envisioned that cap 804 may be removably attached to closure apparatus 800. In such an embodiment, cap 804 may be removed and replaced if any substantial wearing or damage occurs.

Figure 28:
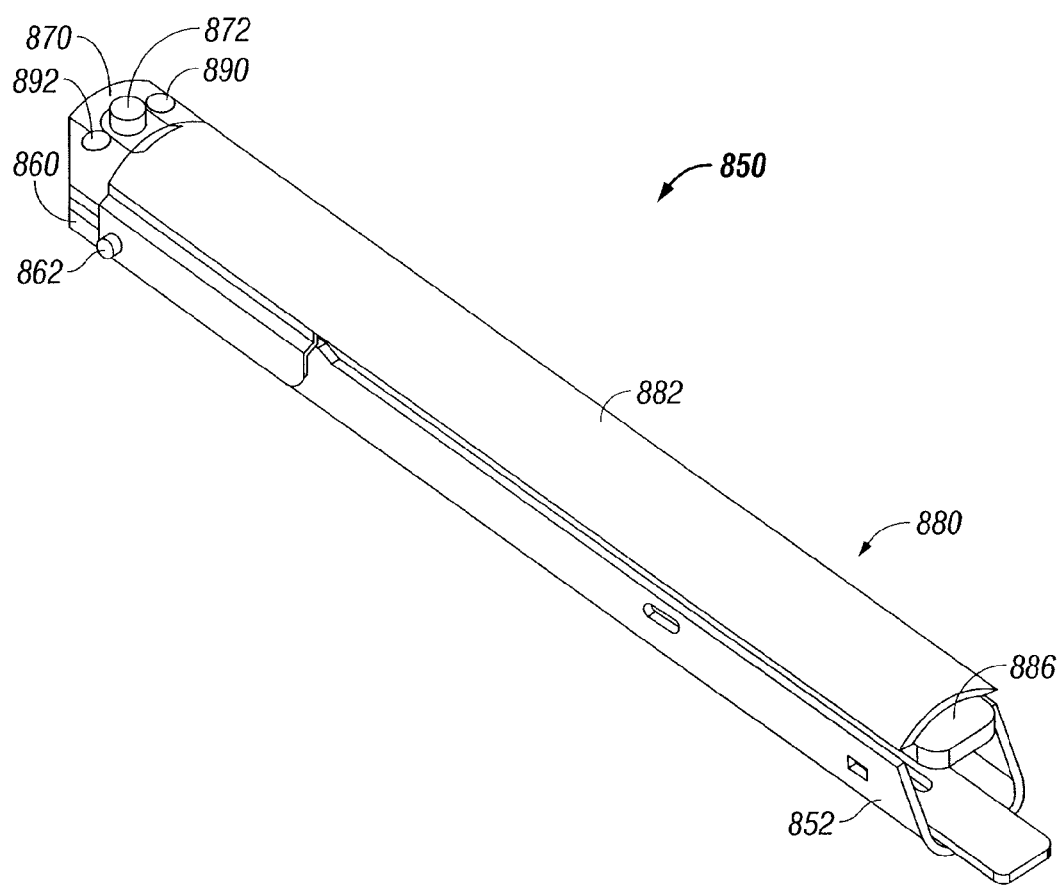
FIG. 28 is a perspective view of a tool assembly in accordance with an embodiment of the present disclosure.

In an embodiment of the present disclosure illustrated in FIGS. 28 and 29, a tool assembly 850 is illustrated. Tool assembly 850 of this embodiment includes a channel 852, a first attachment member 860, a second attachment member 870, an anvil assembly 880, a first attachment rod 890 and a second attachment rod 892. First and second attachment rods 890, 892 provide a strong connection facilitating the elements of tool assembly 850 to remain together.

Channel 852 includes an opening 854 (two openings are illustrated) adjacent its proximal end and first attachment member 860 includes a boss 862 (two bosses are illustrated) extending therefrom. Channel 852 is connectable to first attachment member by placing opening(s) 854 over boss(es) 862, thus providing a pivotal connection therebetween. Although not explicitly illustrated in the present embodiment, channel 852 may house a plurality of surgical fasteners or a staple cartridge.

Anvil assembly 880 includes an anvil cover 882 and an anvil 886. Anvil 886 is configured for mechanical engagement with anvil cover 882, e.g., via a snap-fit connection. An aperture 884 extends at least partially through a portion of anvil cover 882. Aperture 884 is configured to fit over a protrusion 872 disposed on second attachment member 870, thereby providing a connection between anvil assembly 880 and second attachment member 870. Additionally, anvil cover 882 includes at least one opening 888 extending at least partially therethrough in an embodiment of the disclosure. Opening 888 is configured to fit over boss 862 of first attachment member 860. In such an embodiment, anvil assembly 880 may be pivoted with respect to first attachment member 860 and second attachment member 870.

First attachment member 860 includes a first opening 864 and a second opening 866 extending therethrough. Second attachment member 870 also includes a first opening 874 and a second opening 876 extending therethrough (FIG. 29). Further, first attachment member 860 and second attachment member 870 are in mechanical engagement, such that first openings 864, 874 substantially align and second openings 866, 876 substantially align.

To secure first attachment member 860 with second attachment member 870 (and thus channel 852 and anvil assembly 880), first attachment rod 890, or a portion thereof, is inserted through first openings 864 and 874. To further secure the elements of tool assembly 850, second attachment rod 892, or a portion thereof, is inserted through second openings 866 and 876. It is envisioned that first attachment rod 890 and/or second attachment rod 892 are rivets, such as two-part rivets that are tightenable.

In an embodiment of the disclosure, tool assembly 850 is part of a disposable loading unit, which may be able to articulate. Articulation of tool assembly 850 may be facilitated by pivotally attaching tool assembly 850 to a body portion of a surgical instrument via protrusion 874 extending from second attachment member 870 and a link (such as link 710 in FIG. 21). Additionally, a method of assembling tool assembly 850, as described above, is contemplated by the present disclosure.

Embodiments of a surgical instrument having a drive assembly 212' with a cantilevered end member 184 are illustrated in FIGS. 30A-35. With initial reference to FIGS. 30A-30C and 31, drive assembly 212' has a proximal region 194 and a distal region 196 and includes a drive beam 182, end member 184, a flange 186, a sled pushing member 187 and a knife blade 188. Flange 186 is used to reinforce and strengthen end member 184 during the translation through a tool assembly.

Figure 32:
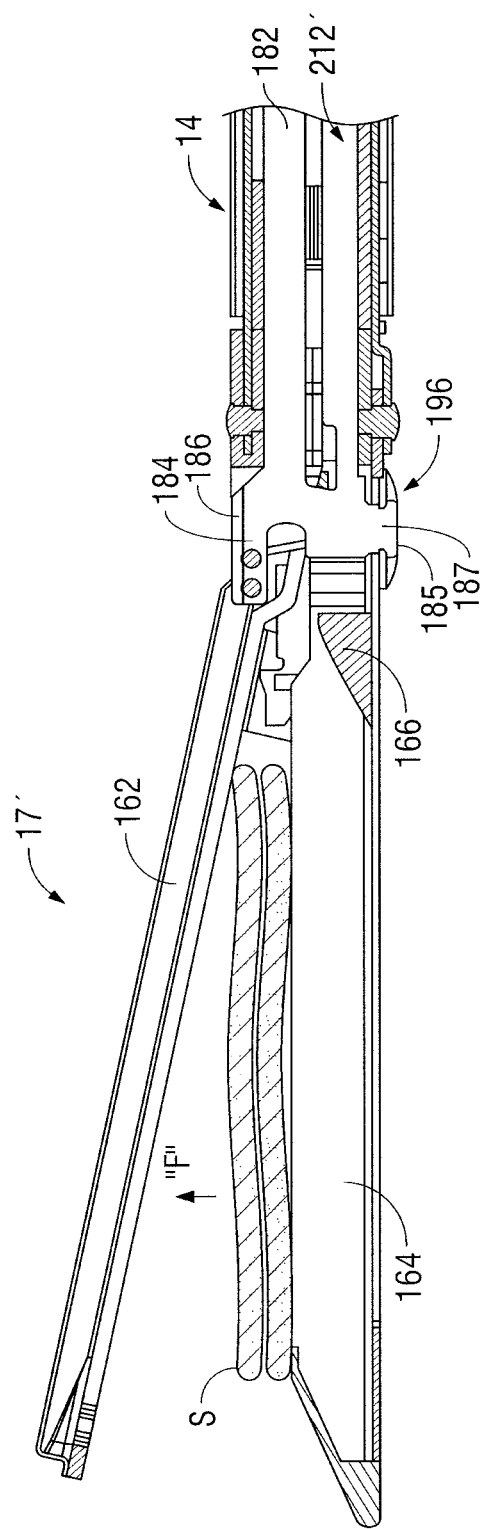
FIG. 32 is a cross-sectional illustration of a tool assembly in connection with the drive assembly of FIGS. 30A-31.
Figure 33:
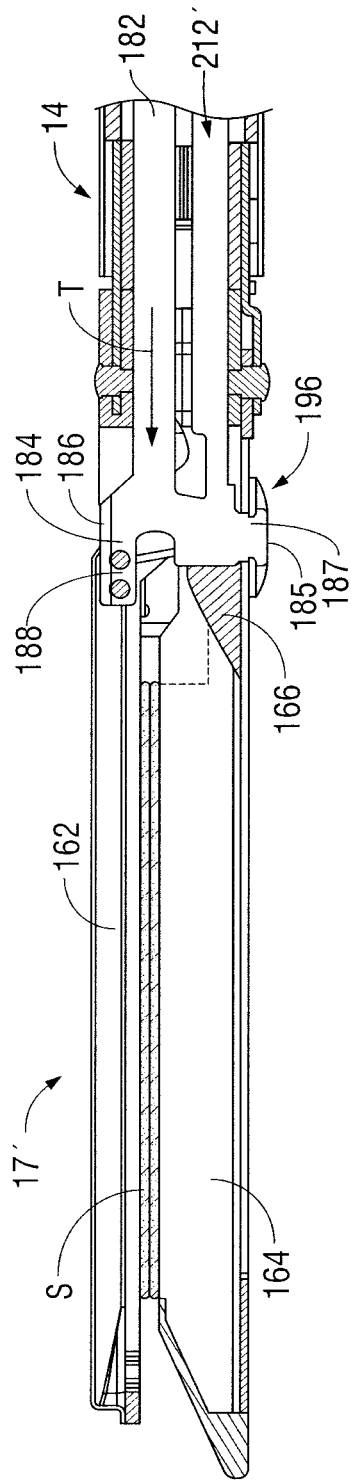
FIG. 33 is a cross-sectional illustration of the drive assembly of FIGS. 30A-31 translating through the tool assembly of FIG. 32.
Figure 34:
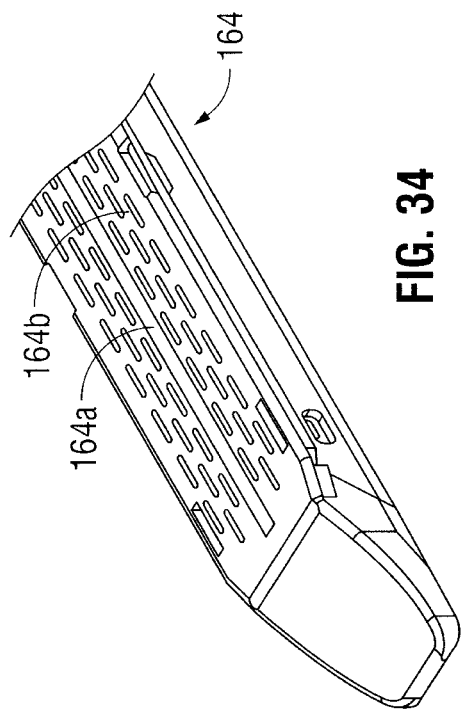
FIG. 34 is an illustration of a portion of a lower jaw of the tool assembly of FIGS. 32 and 33.
Figure 35:
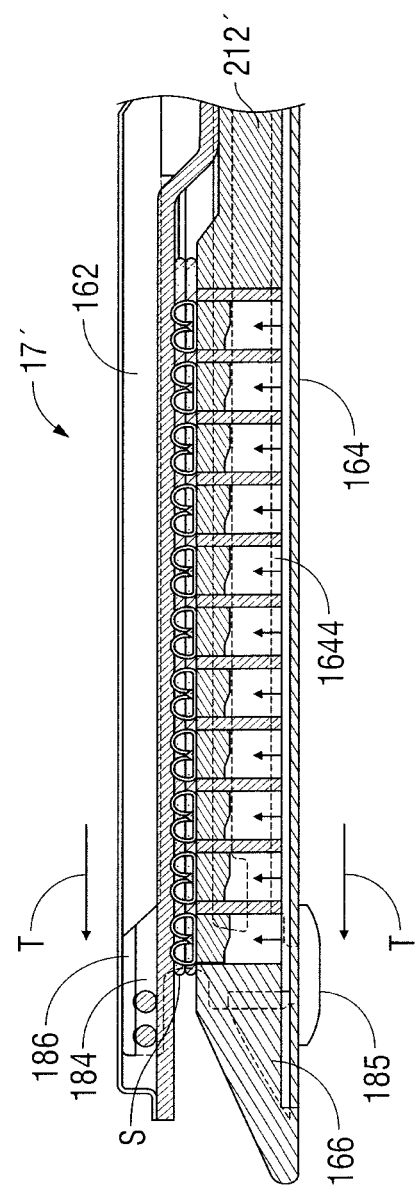
FIG. 35 is a cross-sectional illustration of the drive assembly of FIGS. 30A-31 fully translated into the tool assembly of FIGS. 32-34.

Referring now to FIGS. 32-36B, a tool assembly 17' includes a first jaw 162, a second jaw 164, and an activation sled 166. One of first jaw 162 and second jaw 164 includes an anvil and staple cartridge respectively. First jaw 162 and second jaw 164 may also include jaws for various other types of surgical instruments such as, e.g., scissors and forceps. Second jaw 164 includes a channel 164a dimensioned to accept drive assembly 212' and may include staple slots 164b dimensioned to allow staples to pass therethrough. Upon actuation of movable handle 516 (FIG. 1), drive assembly 212' translates distally in the general direction of arrow "T" as seen in FIGS. 33 and 35. The end member 184 has one or more pins or rollers 189 (see FIGS. 31 and 36A) attached to the upper portion of the end member 184 for engaging the first jaw 162 or the second jaw 164, and a horizontal portion at the lower portion of the end member 184 (not shown). The pins 189 and/or lower horizontal portion can be integrally formed with the end member 184 or attached thereto. As drive assembly 212' translates through tool assembly 17', end member 184 pulls first jaw 162 toward second jaw 164 thereby closing first jaw 162 and clamping a tissue section "S" between first jaw 162 and second jaw 164. In addition, as drive assembly 212' translates through tool assembly 17', sled pushing member 187 comes into contact with and actuates activation sled 166 distally through second jaw 164 thereby firing a series of staples from second jaw 164 through staple slots 1644 into tissue section "S" and into first jaw 162 to crimp the series of staples and secure tissue section "S".

As shown in FIGS. 32, 33 and 35, flange 186 is positioned to reinforce and strengthen end member 184 during translation through tool assembly 17' such that it may carry more load when pulling first jaw 162 into clamping position on thicker tissue. The flange 186 can extend laterally from one or both sides of the end member 184 (i.e., in the direction transverse to a longitudinal axis defined by the drive beam 182). That is, during clamping of tissue section "S," the tissue exerts a force against first jaw 162 in the general direction of arrow "F" in FIG. 32. A distal portion of flange 186 defines a cantilevered portion 191 (see FIG. 31) as distal portion of flange 186 extends distally of a lower portion 185 of the closure apparatus. As can be appreciated, during clamping of the jaws about tissue, flange 186 (e.g., cantilevered portion 191 thereof), which is shown adjacent the thinner and movable portion of tool assembly 17', helps resist the force "F" effected by tissue section "S," while lower portion 185 is shown adjacent the relatively stationary portion of tool assembly 17'. That is, flange 186 provides additional support to the jaw (i.e., illustrated as first jaw 162) that is movable and thinner with respect to the other jaw (i.e., illustrated as jaw 164), and which thus may require the additional support.

Figure 30A:
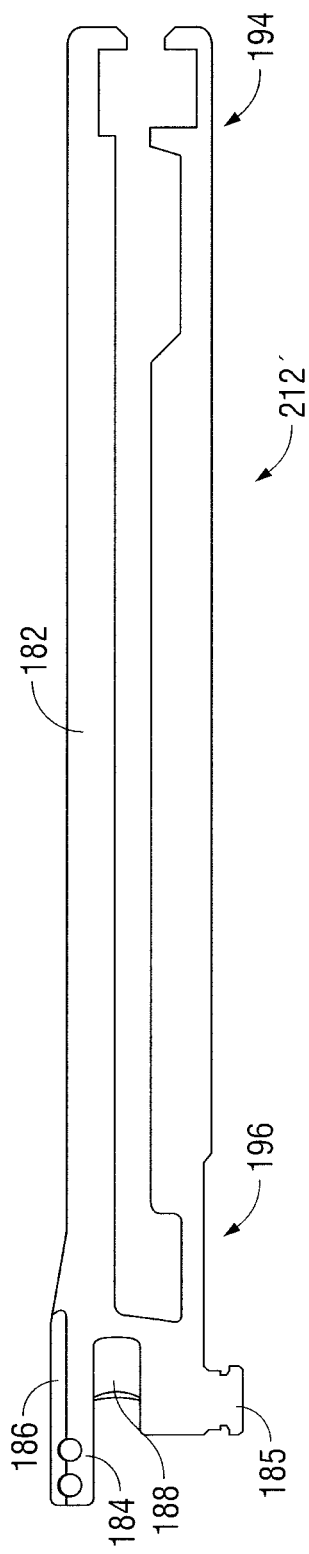
FIG. 30A is a side view of a drive assembly in accordance with an embodiment the present disclosure.
Figure 30B:
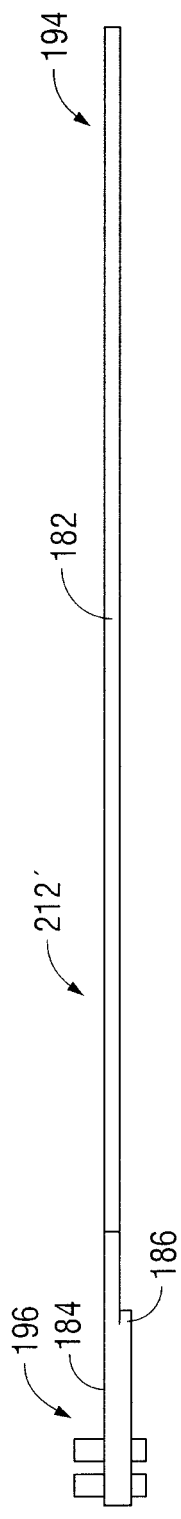
FIG. 30B is a top view of the drive assembly of FIG. 30A.
Figure 30C:
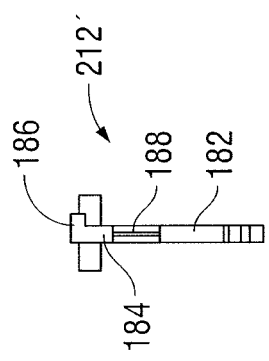
FIG. 30C is a front elevation of the drive assembly of FIG. 30A.
Figure 31:
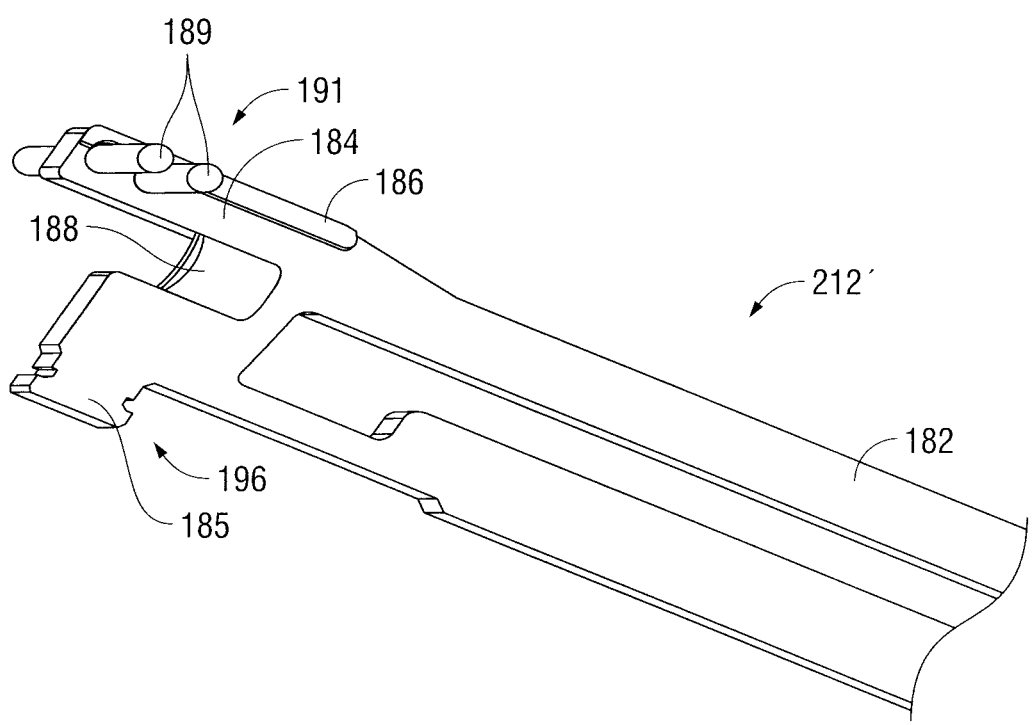
FIG. 31 is a perspective view of the distal end of the drive assembly of FIGS. 30A-30C.

Referring now to FIGS. 30A-30C, end member 184 may be formed as a flat part and flange 186 may be formed by bending a portion of end member 184 from a position parallel to end member 184 to a position at an angle to end member 184. Forming flange 186 in this manner provides for a reinforced and strengthened end member 184 due to the increase in material in a direction transverse to the direction of force "F."

Figure 36A:
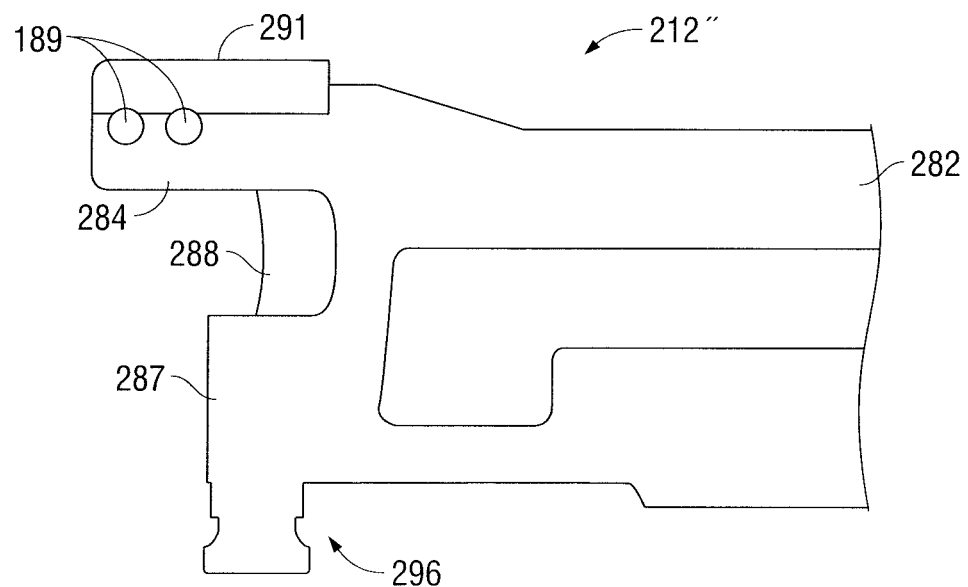
FIG. 36A is a side view of the distal end of a drive assembly in accordance with another embodiment of the present disclosure.
Figure 36B:
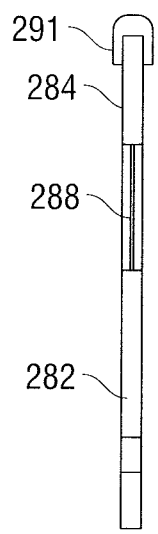
FIG. 36B is a front elevation of the drive assembly of FIG. 36A.

Referring now to FIGS. 36A and 36B, a drive assembly 212''' includes a drive beam 282, an end member 284, a cap 291, a sled pushing member 287 and a knife blade 288. Cap 291 is attached to end member 284 and is used to reinforce and strengthen end member 284 much like flange 186 as described above. Cap 291 may be substantially U-shaped and may include a slot dimensioned to receive end member 284. Cap 291 may also have a length substantially similar to that of end member 284 such that the entire length of end member 284 is reinforced and strengthened. Cap 291 may be attached to end member 284 through various methods including but not limited to, e.g., brazing.

Figure 37A:
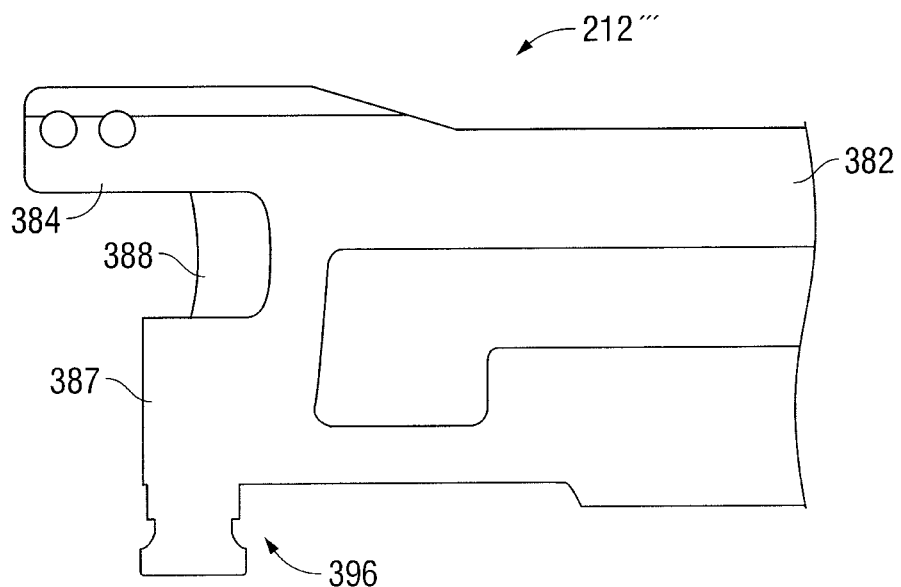
FIG. 37A is a side view of the distal end of a drive assembly in accordance with yet another embodiment of the present disclosure.
Figure 37B:
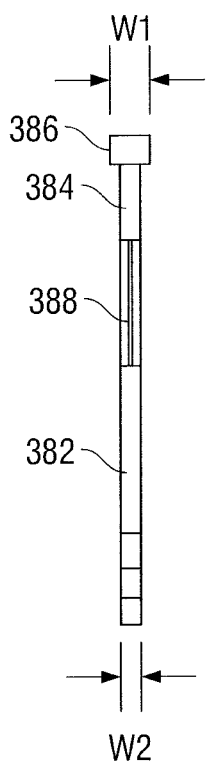
FIG. 37B is a front elevation of the drive assembly of FIG. 37A.

Referring now to FIGS. 37A and 37B, a drive assembly 212''' includes a drive beam 382, an end member 384, a flange 386, a sled pushing member 387 and a knife blade 388. Similar to the above embodiments, flange 386 is used to reinforce and strengthen end member 384. In this embodiment flange 386 is formed by creating a drive assembly having a first larger thickness "W1" and subsequently removing material from drive beam 382 and a portion of end member 384 so as to achieve a second smaller thickness "W2" such that the remaining portion of end member 384 forms flange 386. Flange 386 is formed due to the difference between the original first larger thickness "W1" and the subsequent second smaller thickness "W2." The flange 386 may extend from one or both lateral sides of the end member 384, transversely to a longitudinal axis defined by the drive beam.

The embodiments disclosed in FIGS. 30A-37B serve to strengthen and reinforce the end member of a drive assembly thereby permitting the loading unit to be clamped and fired on thicker particularly over indicated tissue with greatly reduced or eliminated chance of failed clamping or firing which would prevent wound closure. The cantilevered portion 191 of certain embodiments described above allow the drive assembly to engage a cam surface on the first jaw 162 to close the jaws prior to actuating a further aspect of the instrument, such as firing staples.

In the embodiments discussed above in connection with FIGS. 30A through 37B, the end member may be formed integrally with the drive beam, which is configured as a bar. The bar may be formed from one member, or a plurality of sheets. In certain embodiments, the tool assembly is rigidly attached to the shaft of the instrument and doesn't articulate. In certain embodiments, the pins are replaced with a horizontal portion attached to, or integral with, the end member. In certain preferred embodiments, the lower horizontal portion is formed as a separate button with an opening defined by wedge-shaped portions that allow the button to be attached to the lower portion of the end member in an interference fit. Alternatively, the button can be welded or otherwise attached.

It will be understood that various modifications may be made to the embodiments disclosed herein. For example, the above-described lock assembly may be incorporated into a variety of surgical instruments which include loading units and is not limited to use on linear staplers. Further, the loading unit may be configured to receive an insertion tip of surgical instrument in contrast to that disclosed. Therefore, the above description should not be construed as limiting, but merely as exemplifications of various embodiments. Those skilled in the art will envision other modifications within the scope and spirit of the claims appended hereto.

What is claimed is:

1. A surgical instrument comprising:
   a handle assembly;
   an elongate member extending from the handle assembly;
   a tool assembly having a first jaw and a second jaw at a distal portion of the elongate member;
   a drive assembly operatively associated with the handle assembly and configured to translate through the tool assembly upon actuation of the handle assembly, the drive assembly including:
      a drive beam;
      an end member projecting distally from the drive beam and having an upper portion and a lower portion, the upper portion contacting one of the first and second jaws, the end member having a substantially uniform width from the upper portion to the lower portion;
      a cap attachable to the upper portion of the end member, the cap having a different width than the end member, thereby reinforcing the end member; and
   wherein at least one of the first jaw and the second jaw is movable in response to translation of the drive assembly.

2. The surgical instrument of claim 1, wherein the end member has a length in a longitudinal direction of the drive beam and wherein the cap extends the length of the end member.

3. The surgical instrument of claim 2, wherein the upper portion of the end member extends distally in relation to the lower portion of the end member, forming a cantilevered portion.

4. The surgical instrument of claim 1, wherein the cap is attached through brazing.

5. The surgical instrument of claim 1, wherein a first portion of the end member has a first thickness and a second portion of the end member has a second thickness, the first thickness being different than the second thickness.

6. The surgical instrument of claim 1, wherein the first jaw and the second jaw form part of a replaceable loading unit that can be separated from the elongate member.

7. The surgical instrument of claim 1, wherein one of the first jaw and the second jaw is an anvil.

8. The surgical instrument of claim 7, wherein the other of the first jaw and the second jaw is a staple cartridge.

9. The surgical instrument of claim 8, wherein the drive assembly further comprises at least one pin attached to the upper portion of the end member, the pin being positioned to engage one of the anvil and staple cartridge.

10. The surgical instrument of claim 9, wherein the upper portion of the end member forms a cantilevered portion of the end member and wherein the at least one pin is positioned to close the jaws when the drive assembly is translated.

11. The surgical instrument of claim 7, wherein the anvil has a ramped surface that is engaged by the upper portion of the end member.

12. The surgical instrument of claim 11, wherein the staple cartridge has a ramped surface that is engaged by the upper portion of the end member.

13. The surgical instrument of claim 1, wherein the lower portion of the end member has a horizontal portion to engage one of the first jaw and the second jaw.

14. The surgical instrument of claim 1, wherein the upper portion further includes a pin for contacting a surface of the first jaw, the pin extending transversely to a longitudinal axis of the elongate member.

15. The surgical instrument of claim 14, wherein the cap is spaced apart from the surface of the first jaw that is contacted by the pin.

16. The surgical instrument of claim 1, wherein the cap provides additional support to the first jaw as the first jaw moves with respect to the second jaw, thereby resisting forces exerted by tissue disposed between the first and second jaws.

17. The surgical instrument of claim 1, wherein when the upper portion contacts the first jaw such that the first jaw moves relative to the second jaw, the cap is spaced apart from the first jaw.

18. The surgical instrument of claim 1, wherein the upper portion of the end member is at least partially disposed within the cap.

19. The surgical instrument of claim 18, wherein the cap defines an interior chamber, the upper portion of the end member at least partially disposed within the interior chamber.

* * * * *